United States Patent
Yokoyama et al.

(10) Patent No.: US 9,594,189 B2
(45) Date of Patent: Mar. 14, 2017

(54) HIGH REFRACTIVE INDEX CLADDING MATERIAL AND ELECTRO-OPTICAL POLYMER OPTICAL WAVEGUIDE

(75) Inventors: Shiyoshi Yokoyama, Fukuoka (JP); Kazuhiro Yamamoto, Fukuoka (JP); Kei Yasui, Funabashi (JP); Masaaki Ozawa, Funabashi (JP); Keisuke Odoi, Chiyoda-ku (JP)

(73) Assignees: NISSAN CHEMICAL INDUSTRIES, LTD., Tokyo (JP); KYUSHU UNIVERSITY, Fukuoka (JP)

(*) Notice: Subject to any disclaimer, the term of this patent is extended or adjusted under 35 U.S.C. 154(b) by 196 days.

(21) Appl. No.: 14/238,965

(22) PCT Filed: Aug. 13, 2012

(86) PCT No.: PCT/JP2012/070627
§ 371 (c)(1),
(2), (4) Date: Mar. 10, 2014

(87) PCT Pub. No.: WO2013/024840
PCT Pub. Date: Feb. 21, 2013

(65) Prior Publication Data
US 2014/0199038 A1 Jul. 17, 2014

(30) Foreign Application Priority Data
Aug. 15, 2011 (JP) .................... 2011-177559

(51) Int. Cl.
*C08G 73/00* (2006.01)
*G02B 1/04* (2006.01)
(Continued)

(52) U.S. Cl.
CPC ............ *G02B 1/048* (2013.01); *C07D 409/06* (2013.01); *C07F 7/1856* (2013.01); *C08G 61/12* (2013.01);
(Continued)

(58) Field of Classification Search
None
See application file for complete search history.

(56) References Cited

U.S. PATENT DOCUMENTS 7,919,755 B2 * 4/2011 Rahman ................ G02F 1/353
250/341.1
2005/0004253 A1 * 1/2005 Araki .................... G02F 1/3615
522/178

(Continued)

FOREIGN PATENT DOCUMENTS

| JP | A-06-118461 | 4/1994 |
| JP | 08301823 A * | 11/1996 |
| JP | 10333195 A * | 12/1998 |
| JP | A-2001-255566 | 9/2001 |
| JP | 2003049132 A * | 2/2003 |
| JP | A-03-477863 | 10/2003 |
| JP | A-2010-066325 | 3/2010 |

(Continued)

OTHER PUBLICATIONS
Bordeau et al., "Trinaphthylamines as Robust Organic Materials for Two-Photon-Induced Fluorescence", J. Am. Chem. Soc., Nov. 19, 2008, 130 (50), pp. 16836-16837.*
Nov. 20, 2012 International Search Report issued in International Application No. PCT/JP2012/070627.

*Primary Examiner* — Charlie Y Peng
(74) *Attorney, Agent, or Firm* — Oliff PLC

(57) ABSTRACT

There is provided an optical waveguide which has appropriate orientation properties, a production process of which is simple so as to be suitable for producing an electro-optical element, and is able to reduce power consumption of the element due to excellent electro-optical properties, and further can be formed into a thin film and be layered; and a material for the optical waveguide. A cladding material of an optical waveguide, characterized by comprising a polymer compound including a triarylamine structure, and a nonlinear optical compound; and an optical waveguide produced by using the cladding material.

11 Claims, 1 Drawing Sheet

(51) Int. Cl.

| | | |
|---|---|---|
| *C07D 409/06* | (2006.01) | |
| *C08G 61/12* | (2006.01) | |
| *G02F 1/361* | (2006.01) | |
| *G02F 1/065* | (2006.01) | |
| *G02F 1/365* | (2006.01) | |
| *G03F 7/00* | (2006.01) | |
| *C07F 7/18* | (2006.01) | |
| *G02F 1/00* | (2006.01) | |

(52) U.S. Cl.
CPC .............. *G02F 1/065* (2013.01); *G02F 1/365* (2013.01); *G02F 1/3611* (2013.01); *G02F 1/3614* (2013.01); *G03F 7/0005* (2013.01); *C08G 2261/3162* (2013.01); *C08G 2261/90* (2013.01); *G02F 1/0018* (2013.01)

(56) References Cited

U.S. PATENT DOCUMENTS

| | | | |
|---|---|---|---|
| 2010/0096603 A1* | 4/2010 | Wang | C09K 15/16 252/587 |
| 2013/0128339 A1* | 5/2013 | Gu | G02F 1/0063 359/299 |
| 2014/0133000 A1* | 5/2014 | Choi | G03H 1/26 359/32 |

FOREIGN PATENT DOCUMENTS

| | | |
|---|---|---|
| JP | A-2010-139994 | 6/2010 |
| WO | WO 2011/065395 A1 | 6/2011 |

\* cited by examiner

HIGH REFRACTIVE INDEX CLADDING MATERIAL AND ELECTRO-OPTICAL POLYMER OPTICAL WAVEGUIDE

TECHNICAL FIELD

The present invention relates to an optical waveguide containing an organic nonlinear optical compound that is used for an optical switch, optical information processing such as light modulation, optical communications, and the like.

BACKGROUND ART

Devices such as an optical modulator and an optical switch utilize nonlinear optical effects, and among these particularly an electro-optical effect that is a change in refractive index in response to an electric field. Conventionally, as nonlinear optical materials exhibiting this effect, inorganic materials such as lithium niobate and potassium dihydrogen phosphate have been widely used. To satisfy requirements such as higher nonlinear optical performance and production cost reduction, organic nonlinear optical materials are attracting attention and studies for the practical use thereof are actively carried out.

There are growing expectations for development of polymer materials having extremely excellent electro-optical properties compared to those of conventional inorganic materials to fabricate a super high-speed modulation device or to implement a low power consumption device technology, in particular. These polymer materials cause organic nonlinear optical compounds to uniformly disperse in a polymer matrix or to bind to polymer side chains, and orient the compound molecules to give rise to the electro-optical properties. As such a nonlinear optical compound, a push-pull compound having a π-conjugated chain, one end of which is electron donative and the other end of which is electron attractive, is used.

Examples of a known method for production thereof include a method of applying a polymer material onto a substrate having an oriented film on a surface thereof to use the substrate orientation of the oriented film, and an electric field poling method in which a polymer material heated to near the glass transition temperature or higher is oriented by applying voltage thereto with a pair of electrodes or corona discharge in the air. Among these, the electric field poling method is preferred from the viewpoint of simplicity of apparatus and the high degree of orientation of nonlinear optical compounds.

An optical waveguide required when a nonlinear optical material is used for a light propagation-type device is formed in a layered structure, in which a polymer core portion containing a nonlinear optical compound and cladding portions having a refractive index smaller than that of the core portion on and under or around the core portion are formed. As the nonlinearity of the nonlinear optical compound contained in the core portion becomes higher, the electrical resistivity of the core portion tends to become lower. Accordingly, the electrical resistivity of the cladding portions tends to be relatively high compared to that of the core portion, and consequently, voltage cannot be efficiently applied to the core portion and appropriate electro-optical properties cannot be obtained.

To solve this issue, Patent Document 1 describes a method in which a polymer compound having an alkylammonium group is added into a cladding material to reduce the resistance value of the cladding portion and thus improve the poling efficiency.

PRIOR ART DOCUMENT

Patent Document

Patent Document 1: Japanese Patent No. 3477863

SUMMARY OF THE INVENTION

Problems to be Solved by the Invention

By the method described above, appropriate orientation properties still cannot be obtained. A polymer cladding material, a production process of which is simple so as to be suitable for producing an electro-optical element and that provides excellent electro-optical properties contributing to the reduction of power consumption of the element and can be formed into a thin film and be layered, and an optical waveguide using the cladding material are expected to be developed.

Means for Solving the Problems

As a result of repeated intensive studies to achieve an object described above, the inventors of the present invention found that blending a nonlinear optical compound that had been contained only in a core portion also into a cladding portion can reduce the resistance value of the cladding significantly below the resistance value of the core portion, and completed the present invention.

More specifically, the present invention relates to, as a first aspect, a cladding material of an optical waveguide, characterized by comprising: a polymer compound including a triarylamine structure; and a nonlinear optical compound.

As a second aspect, the present invention relates to the cladding material according to the first aspect, in which the nonlinear optical compound is a compound having a tricyano-bonded furan ring.

As a third aspect, the present invention relates to the cladding material according to the second aspect, in which the compound having the tricyano-bonded furan ring is a compound of formula (1):

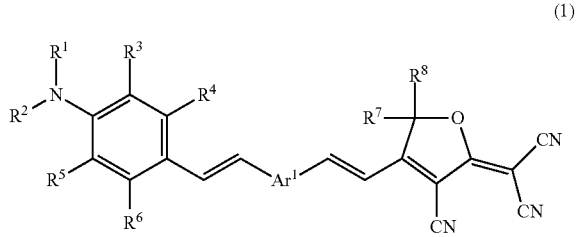

(1)

(in the formula, $R^1$ and $R^2$ are each independently a hydrogen atom, a $C_{1-10}$ alkyl group optionally having a substituent, or a $C_{6-10}$ aryl group; $R^3$ to $R^6$ are each independently a hydrogen atom, a $C_{1-10}$ alkyl group, a hydroxy group, a $C_{1-10}$ alkoxy group, a $C_{2-11}$ alkylcarbonyloxy group, a $C_{6-10}$ aryloxy group, a $C_{7-11}$ arylcarbonyloxy group, a silyloxy group having a $C_{1-6}$ alkyl group and/or a phenyl group, or a halogen atom; $R^7$ and $R^8$ are each independently a hydrogen atom, a $C_{1-5}$ alkyl group, a $C_{1-5}$ haloalkyl group, or a $C_{6-10}$ aryl group; and $Ar^1$ is a divalent organic group of formula ($Ar^1$-a) or formula ($Ar^1$-b):

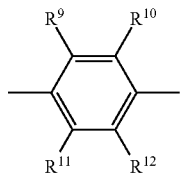
($Ar^1$-a)

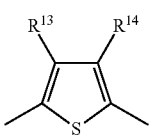
($Ar^1$-b)

(in the formulae, $R^9$ to $R^{14}$ are each independently a hydrogen atom, a $C_{1-10}$ alkyl group optionally having a substituent, or a $C_{6-10}$ aryl group)).

As a fourth aspect, the present invention relates to the cladding material according to the first aspect, in which the polymer compound including the triarylamine structure has a repeating unit of formula (2) or formula (3):

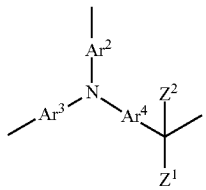
(2)

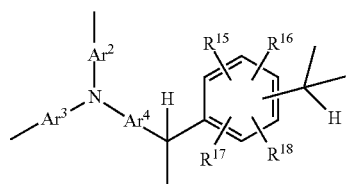
(3)

(in formula (2) and formula (3), $Ar^2$ to $Ar^4$ are each independently any one of divalent organic groups of formulae (4) to (8) below; in formula (2), $Z^1$ and $Z^2$ are each independently a hydrogen atom, a $C_{1-5}$ alkyl group, or any one of monovalent organic groups of formulae (9) to (12) below (provided that $Z^1$ and $Z^2$ are not simultaneously the alkyl groups); and in formula (3), $R^{15}$ to $R^{18}$ are each independently a hydrogen atom, a $C_{1-5}$ alkyl group, a $C_{1-5}$ hydroxyalkyl group, a $C_{1-5}$ alkoxy group, or a halogen atom),

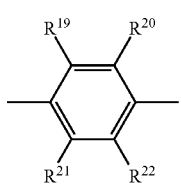
(4)

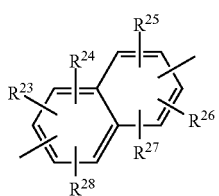
(5)

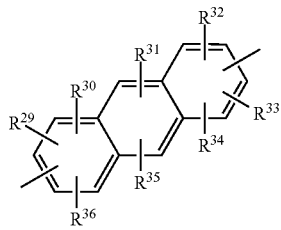
(6)

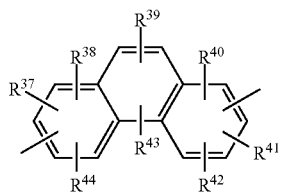
(7)

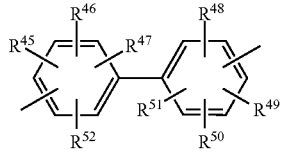
(8)

(in the formulae, $R^{19}$ to $R^{52}$ are each independently a hydrogen atom, a $C_{1-5}$ alkyl group, an epoxy group, a carboxy group, a hydroxy group, a $C_{1-5}$ alkoxy group, or a halogen atom),

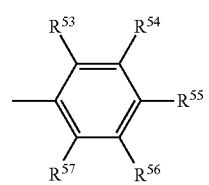
(9)

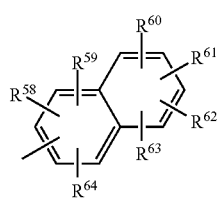
(10)

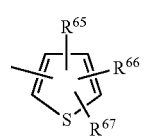
(11)

-continued

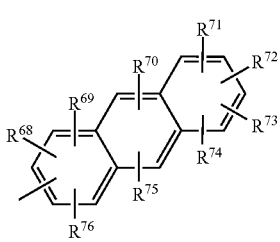
(12)

(in the formulae, $R^{53}$ to $R^{76}$ are each independently a hydrogen atom, a halogen atom, a $C_{1-5}$ alkyl group, a $C_{1-5}$ hydroxyalkyl group, a $C_{1-5}$ haloalkyl group, a phenyl group, an $OR^{77}$ group, a $COR^{77}$ group, a $COOR^{77}$ group, or an $NR^{77}R^{78}$ group (in these formulae, $R^{77}$ and $R^{78}$ are each independently a hydrogen atom, a $C_{1-5}$ alkyl group, a $C_{1-5}$ hydroxyalkyl group, a $C_{1-5}$ haloalkyl group, or a phenyl group)).

As a fifth aspect, the present invention relates to the cladding material according to the fourth aspect, in which the repeating unit is represented by formula (13):

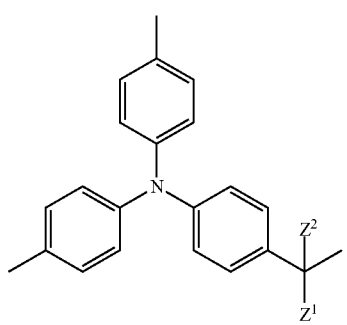
(13)

(in the formula, $Z^1$ and $Z^2$ are the same as $Z^1$ and $Z^2$ above).

As a sixth aspect, the present invention relates to the cladding material according to the fifth aspect, in which the $Z^1$ is a monovalent organic group of formula (9), and the $Z^2$ is a hydrogen atom.

As a seventh aspect, the present invention relates to an optical waveguide comprising: a core; and a cladding that surrounds an entire periphery of the core and has a refractive index smaller than a refractive index of the core, in which the cladding is formed of the cladding material as described in any one of the first aspect to the sixth aspect.

As an eighth aspect, the present invention relates to the optical waveguide according to the seventh aspect, in which the core contains a nonlinear optical compound having a tricyano-bonded furan ring of formula (1) or a derivative of the nonlinear optical compound, (1)

(in the formula, $R^1$ and $R^2$ are each independently a hydrogen atom, a $C_{1-10}$ alkyl group optionally having a substituent, or a $C_{6-10}$ aryl group; $R^3$ to $R^6$ are each independently a hydrogen atom, a $C_{1-10}$ alkyl group, a hydroxy group, a $C_{1-10}$ alkoxy group, a $C_{2-11}$ alkylcarbonyloxy group, a $C_{6-10}$ aryloxy group, a $C_{7-11}$ arylcarbonyloxy group, a silyloxy group having a $C_{1-6}$ alkyl group and/or a phenyl group, or a halogen atom; $R^7$ and $R^8$ are each independently a hydrogen atom, a $C_{1-5}$ alkyl group, a $C_{1-5}$ haloalkyl group, or a $C_{6-10}$ aryl group; and $Ar^1$ is a divalent organic group of formula ($Ar^1$-a) or formula ($Ar^1$-b):

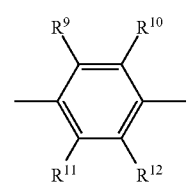
($Ar^1$-a)

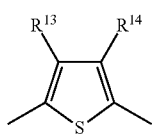
($Ar^1$-b)

(in the formulae, $R^9$ to $R^{14}$ are each independently a hydrogen atom, a $C_{1-10}$ alkyl group optionally having a substituent, or a $C_{6-10}$ aryl group)).

As a ninth aspect, the present invention relates to a production method of the optical waveguide as described in the eighth aspect having the core and the cladding that surrounds the periphery of the core and has a refractive index smaller than a refractive index of the core, the production method comprising:

a step of forming a lower cladding using the cladding material as described in any one of the first aspect to the sixth aspect;

a step of forming on the lower cladding the core containing the nonlinear optical compound having the tricyano-bonded furan ring of formula (1) or the derivative of the nonlinear optical compound as described in the eight aspect; and a step of forming an upper cladding on the core using the cladding material as described in any one of the first aspect to the sixth aspect, in which the production method includes, before and/or after the step of forming of the upper cladding, a step of performing a polarization orientation process on the nonlinear optical compound or the derivative of the nonlinear optical compound contained in the core.

As a tenth aspect, the present invention relates to a production method of a ridge-type optical waveguide that is a production method of the optical waveguide as described in the eighth aspect having the core and the cladding that surround the periphery of the core and has a refractive index smaller than a refractive index of the core, the production method comprising:

a step of forming a lower cladding using the cladding material as described in any one of the first aspect to the sixth aspect;

a step of forming a resist layer having photosensitivity to ultraviolet rays on the lower cladding, radiating ultraviolet light onto a surface of the resist layer through a photomask and carrying out development to form a mask pattern of the core, transferring a core pattern to the lower cladding using the mask pattern as a mask, and removing the resist layer;

a step of forming on the lower cladding the core containing the nonlinear optical compound having the tricyano-bonded furan ring of formula (1) or the derivative of the nonlinear optical compound as described in the eight aspect; and a step of forming an upper cladding on the core using the cladding material as described in any one of the first aspect to the sixth aspect, in which the production method includes, before and/or after the step of forming of the upper cladding, a step of performing a polarization orientation process on the nonlinear optical compound or the derivative of the nonlinear optical compound contained in the core.

As an eleventh aspect, the present invention relates to the production method according to the ninth aspect or the tenth aspect, characterized in that the polarization orientation process is an electric field applying process with electrodes.

As a twelfth aspect, the present invention relates to a polymer compound having a repeating unit of formula (2) or formula (3):

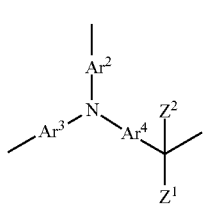
(2)

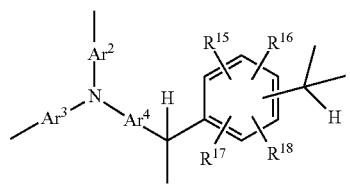
(3)

(in formula (2) and formula (3), $Ar^2$ to $Ar^4$ are each independently any one of divalent organic groups of formulae (4) to (8) below; in formula (2), $Z^1$ and $Z^2$ are each independently a hydrogen atom, a $C_{1-5}$ alkyl group, or any one of monovalent organic groups of formulae (9) to (12) below (provided that $Z^1$ and $Z^2$ are not simultaneously the alkyl groups); and in formula (3), $R^{15}$ to $R^{18}$ are each independently a hydrogen atom (provided that $R^{15}$ to $R^{18}$ are not simultaneously hydrogen atoms) or a $C_{1-5}$ hydroxyalkyl group),

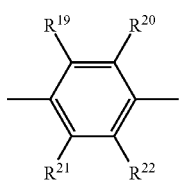
(4)

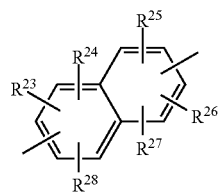
(5)

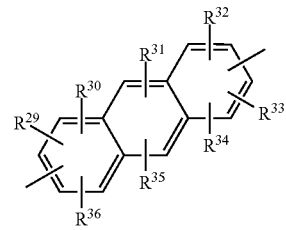
(6)

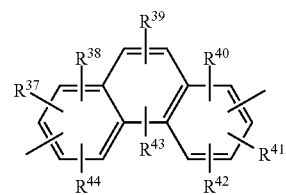
(7)

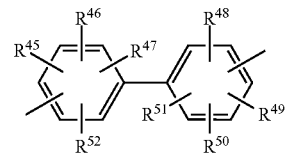
(8)

(in the formulae, $R^{19}$ to $R^{52}$ are each independently a hydrogen atom, a $C_{1-5}$ alkyl group, an epoxy group, a carboxy group, a hydroxy group, a $C_{1-5}$ alkoxy group, or a halogen atom),

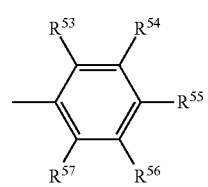
(9)

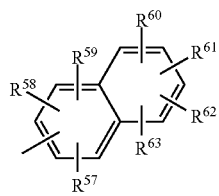
(10)

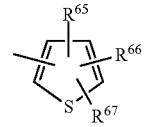
(11)

-continued

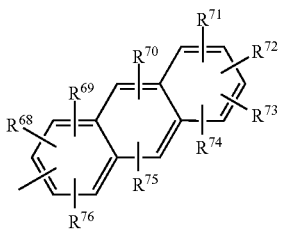
(12)

(in the formulae, $R^{53}$ to $R^{76}$ are each independently a hydrogen atom (provided that $R^{53}$ to $R^{57}$, $R^{58}$ to $R^{64}$, $R^{65}$ to $R^{67}$, or $R^{68}$ to $R^{76}$ are not simultaneously hydrogen atoms), a $C_{1-5}$ hydroxyalkyl group, an $OR^{77}$ group, a $COR^{77}$ group, a $COOR^{77}$ group, or an $NR^{77}R^{78}$ group (in these formulae, $R^{77}$ and $R^{78}$ are each independently a hydrogen atom (provided that $R^{77}$ and $R^{78}$ are not simultaneously hydrogen atoms) or a $C_{1-5}$ hydroxyalkyl group)).

As a thirteenth aspect, the present invention relates to the polymer compound according to the twelfth aspect, in which the repeating unit is represented by formula (13):

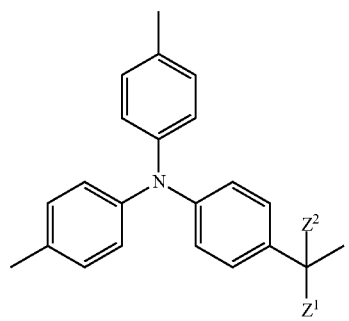
(13)

(in the formula, $Z^1$ and $Z^2$ are the same as $Z^1$ and $Z^2$ above).

As a fourteenth aspect, the present invention relates to the polymer compound according to the thirteenth aspect, in which the $Z^1$ is a monovalent organic group of formula (9), and the $Z^2$ is a hydrogen atom.

Effects of the Invention

The cladding material of the present invention has a very low resistivity, and thus can form an optical waveguide that enables simple and efficient electric field application to a core portion when used as a cladding of the optical waveguide.

MODES FOR CARRYING OUT THE INVENTION

Figure 1:
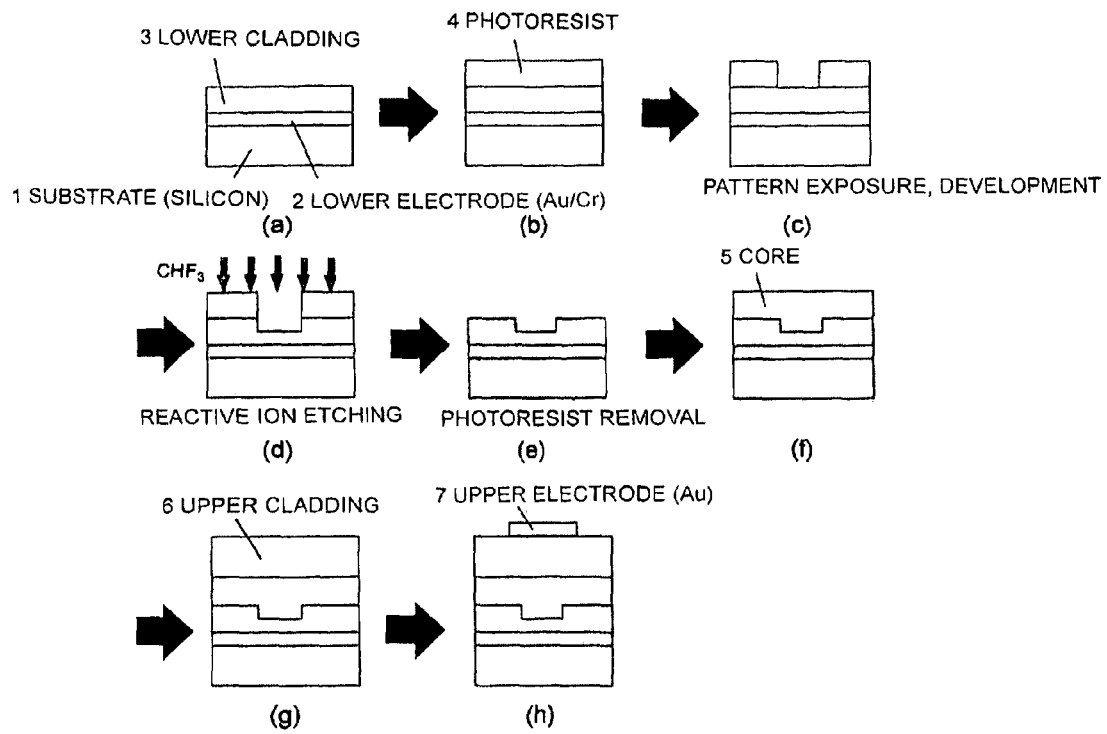
FIG. 1 shows diagrams illustrating a process chart that indicates a production process of a ridge-type optical waveguide produced in Examples.

The present invention is directed to a cladding material of an optical waveguide that is characterized by containing a polymer compound including a triarylamine structure and a nonlinear optical compound. The present invention is also directed to an optical waveguide produced by using the cladding material and a method for producing the optical waveguide.

The present invention will be described in further detail below.

[Cladding Material]

<Polymer Compound Including Triarylamine Structure>

The polymer compound including a triarylamine structure used in the present invention is not particularly limited, but is preferably a polymer compound having a repeating unit of formula (2) or formula (3) below that includes a triarylamine skeleton as a branch point.

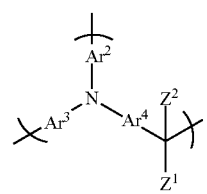
(2)

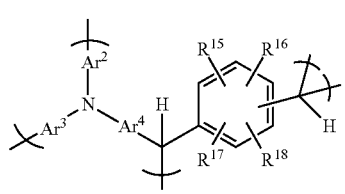
(3)

In formula (2) and formula (3), $Ar^2$ to $Ar^4$ are each independently any one of divalent organic groups of formulae (4) to (8).

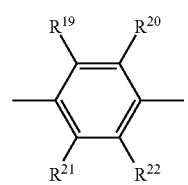
(4)

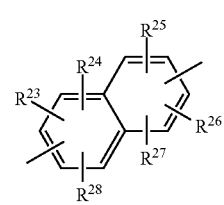
(5)

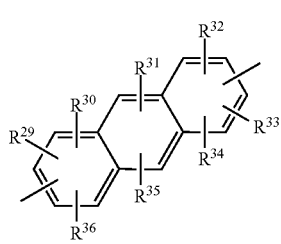
(6)

-continued

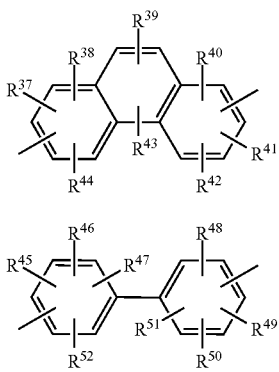
(7)

(8)

In formulae (4) to (8), $R^{19}$ to $R^{52}$ are each independently a hydrogen atom, a $C_{1-5}$ alkyl group, an epoxy group, a carboxy group, a hydroxy group, a $C_{1-5}$ alkoxy group, or a halogen atom.

The $C_{1-5}$ alkyl group herein may have a branched structure or a cyclic structure, and examples thereof include a methyl group, an ethyl group, an n-propyl group, an isopropyl group, a cyclopropyl group, an n-butyl group, an isobutyl group, a sec-butyl group, a tert-butyl group, an n-pentyl group, a neopentyl group, and a cyclopentyl group.

The $C_{1-5}$ alkoxy group may have a branched structure or a cyclic structure, and examples thereof include a methoxy group, an ethoxy group, an n-propoxy group, an isopropoxy, a cyclopropoxy group, an n-butoxy group, an isobutoxy group, a sec-butoxy group, a tert-butoxy group, an n-pentyloxy group, a neopentyloxy group, and a cyclopentyloxy group.

Examples of the halogen atom include a fluorine atom, a chlorine atom, a bromine atom, and an iodine atom.

For the $Ar^2$ to $Ar^4$, a substituted or unsubstituted phenylene group of formula (4) is preferred among the foregoing, and particularly the phenylene group, in which $R^{19}$ to $R^{22}$ are all hydrogen atoms, is preferred.

In formula (2), $Z^1$ and $Z^2$ are each independently a hydrogen atom, a $C_{1-5}$ alkyl group, or any one of monovalent organic groups of formulae (9) to (12) below. Note that $Z^1$ and $Z^2$ are not simultaneously the alkyl groups.

Examples of the $C_{1-5}$ alkyl group herein include the same groups as those recited for the $R^{19}$ to $R^{52}$.

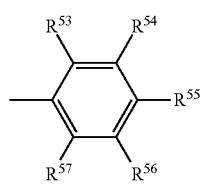
(9)

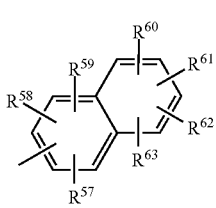
(10)

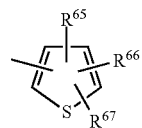
(11)

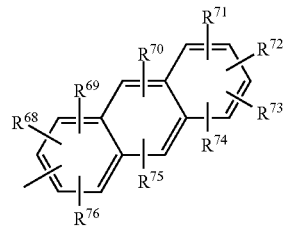
(12)

In formulae (9) to (12), $R^{53}$ to $R^{76}$ are each independently a hydrogen atom, a halogen atom, a $C_{1-5}$ alkyl group, a $C_{1-5}$ hydroxyalkyl group, a $C_{1-5}$ haloalkyl group, a phenyl group, an $OR^{77}$ group, a $COR^{77}$ group, a $COOR^{77}$ group, or an $NR^{77}R^{78}$ group. In these formulae, $R^{77}$ and $R^{78}$ are each independently a hydrogen atom, a $C_{1-5}$ alkyl group, a $C_{1-5}$ hydroxyalkyl group, a $C_{1-5}$ haloalkyl group, or a phenyl group.

Examples of the $C_{1-5}$ alkyl group herein include the same groups as those recited for the $R^{19}$ to $R^{52}$.

The $C_{1-5}$ hydroxyalkyl group may have a branched structure or a cyclic structure, and examples thereof include a hydroxymethyl group, a 2-hydroxyethyl group, a 2-hydroxypropyl group, a 1-hydroxypropane-2-yl group, a 2-hydroxycyclopropyl group, a 4-hydroxybutyl group, a 5-hydroxypentyl group, and a 1-hydroxycyclopentyl group.

The $C_{1-5}$ haloalkyl group may have a branched structure or a cyclic structure, and examples thereof include a fluoromethyl group, a trifluoromethyl group, a bromodifluoromethyl group, a 2-chloroethyl group, a 2-bromoethyl group, a 1,1-difluoroethyl group, a 2,2,2-trifluoroethyl group, a 1,1,2,2-tetrafluoroethyl group, a 2-chloro-1,1,2-trifluoroethyl group, a pentafluoroethyl group, a 3-bromopropyl group, a 2,2,3,3-tetrafluoropropyl group, a 1,1,2,3,3,3-hexafluoropropyl group, a 1,1,1,3,3,3-hexafluoropropane-2-yl group, a 3-bromo-2-methylpropyl group, a 2,2,3,3-tetrafluorocyclopropyl group, a 4-bromobutyl group, a perfluoropentyl group, and a perfluorocyclopentyl group.

Examples of the halogen atom include the same atoms as those recited for the $R^{19}$ to $R^{52}$.

The $Z^1$ and $Z^2$ are each independently preferred to be a hydrogen atom, a 2-thienyl group, a 3-thienyl group, or a substituted or unsubstituted phenyl group of formula (9). It is more preferable that either one of $Z^1$ and $Z^2$ be a hydrogen atom and the other be a hydrogen atom, a 2-thienyl group, a 3-thienyl group, or a substituted or unsubstituted phenyl group of formula (9), particularly a hydroxyalkoxyphenyl group, in which any one of $R^{53}$ to $R^{57}$ is a hydroxyalkoxy group.

In formula (3), $R^{15}$ to $R^{18}$ are each independently a hydrogen atom, a $C_{1-5}$ alkyl group, a $C_{1-5}$ hydroxyalkyl group, a $C_{1-5}$ alkoxy group, or a halogen atom.

Examples of the $C_{1-5}$ alkyl group, the $C_{1-5}$ alkoxy group, and the halogen atom herein include the same groups and atoms as those recited for the $R^{19}$ to $R^{52}$.

Examples of the $C_{1-5}$ hydroxyalkyl group include the same groups as those recited for the $R^{53}$ to $R^{76}$.

In the present invention, the polymer compound including the triarylamine structure desirably has at least one repeating unit out of four structures of formula (14):

(14)

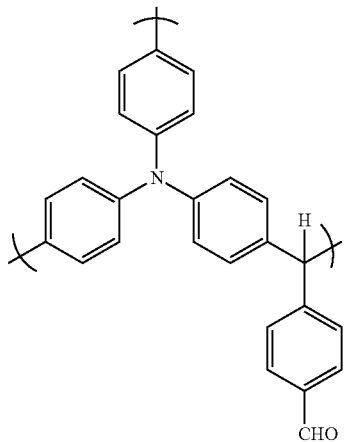

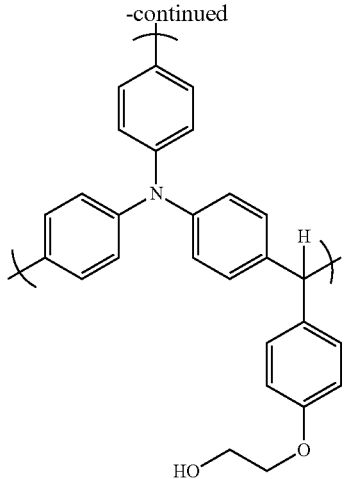

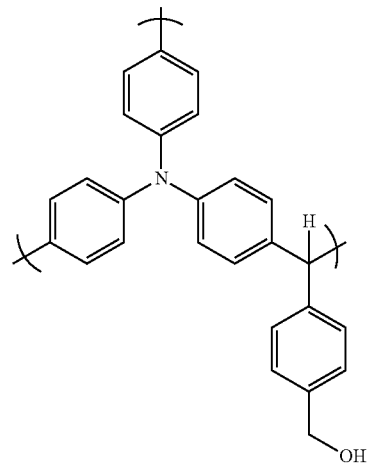

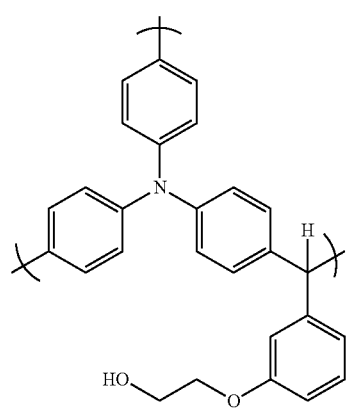

The present invention is directed also to a polymer compound having the repeating unit of formula (2) or formula (3), preferably a polymer compound having the repeating unit of formula (13) and a polymer compound having at least one of the repeating units of formula (14).

More specifically, a polymer compound to which the present invention is directed is the polymer compound having the repeating unit of formula (2) or formula (3). For this polymer compound, in formula (2) and formula (3), $Ar^2$ to $Ar^4$ are each independently any one of divalent organic groups of formulae (4) to (8) (in formulae (4) to (8), $R^{19}$ to $R^{52}$ are each independently a hydrogen atom, a $C_{1-5}$ alkyl group, an epoxy group, a carboxy group, a hydroxy group, a $C_{1-5}$ alkoxy group, or a halogen atom); in formula (2), $Z^1$ and $Z^2$ are each independently a hydrogen atom, a $C_{1-5}$ alkyl group, or any one of monovalent organic groups of formulae (9) to (12) (in formulae (9) to (12), $R^{53}$ to $R^{76}$ are each independently a hydrogen atom (provided that $R^{53}$ to $R^{57}$, $R^{58}$ to $R^{64}$, $R^{65}$ to $R^{67}$, or $R^{68}$ to $R^{76}$ are not simultaneously hydrogen atoms), a $C_{1-5}$ hydroxyalkyl group, an $OR^{77}$ group, a $COR^{77}$ group, a $COOR^{77}$ group, or an $NR^{77}R^{78}$ group (in these formulae, $R^{77}$ and $R^{78}$ are each independently a hydrogen atom (provided that $R^{77}$ and $R^{78}$ are not simultaneously hydrogen atoms) or a $C_{1-5}$ hydroxyalkyl group) (provided that $Z^1$ and $Z^2$ are not simultaneously the alkyl groups); and in formula (3), $R^{15}$ to $R^{18}$ are each independently a hydrogen atom (provided that $R^{15}$ to $R^{18}$ are not simultaneously hydrogen atoms) or a $C_{1-5}$ hydroxyalkyl group.

Specific examples of the respective groups herein include those recited above.

The average molecular weight of the polymer compound including the triarylamine structure used in the present invention is not particularly limited, but the weight-average molecular weight is preferably 1,000 to 2,000,000. When the polymer compound has a weight-average molecular weight of 1,000 or higher and is used as a cladding material, film quality can be made more uniform in formation of a thin film. When having a weight-average molecular weight of 2,000,000 or lower, the polymer compound can be easily handled while the solubility in solvent does not significantly decrease. The weight-average molecular weight is more preferably 2,000 to 1,000,000.

The weight-average molecular weight in the present invention is a measured value by gel permeation chromatography (in terms of polystyrene).

<Production of Polymer Compound Including Triarylamine Structure>

The polymer compound can be obtained by polycondensing a triarylamine compound and an aldehyde compound under acidic conditions.

Examples of the aldehyde compound used for production of the polymer compound including the triarylamine structure include saturated aliphatic aldehydes such as formaldehyde, paraformaldehyde, acetaldehyde, propionaldehyde, butyraldehyde, isobutyraldehyde, n-valeraldehyde, 2-methylbutyraldehyde, 3-methyl-2-butenal, and hexylaldehyde; heterocyclic aldehydes such as thiophene aldehyde; and aromatic aldehydes such as benzaldehyde, tolyl aldehyde, hydroxymethylbenzaldehyde, trifluoromethylbenzaldehyde, phenylbenzaldehyde, salicylaldehyde, anisaldehyde, (2-hydroxyethoxy)benzaldehyde, terephthalaldehyde, acetylbenzaldehyde, formylbenzoic acid, formylbenzoic acid methyl, aminobenzaldehyde, N,N-dimethylaminobenzaldehyde, N,N-diphenylaminobenzaldehyde, naphthylaldehyde, and anthrylaldehyde.

Examples of a usable acid catalyst used in production of the polymer compound may include mineral acids such as sulfuric acid, phosphoric acid, and perchloric acid; organic sulfonic acids such as p-toluenesulfonic acid and p-toluenesulfonic acid monohydrate; or carboxylic acids such as formic acid and oxalic acid.

The amount of use of the acid catalyst is selected depending on the type thereof, and is generally 0.001 to 10,000 parts by mass, preferably 0.01 to 1,000 parts by mass, and more preferably 0.1 to 100 parts by mass with respect to 100 parts by mass of the triarylamine compound.

The condensation reaction above can be performed without solvent but generally performed with solvent. Any solvent can be used unless it inhibits the reaction. Examples of the solvent include cyclic ethers such as tetrahydrofuran (THF) and 1,4-dioxane; amides such as N,N-dimethylformamide (DMF), N,N-dimethylacetamide (DMAc), and N-methyl-2-pyrolidone (NMP); ketones such as isobutyl methyl ketone and cyclohexanone; halogenated hydrocarbons such as methylene chloride, chloroform, 1,2-dichloroethane, and chlorobenzene; and aromatic hydrocarbons such as benzene, toluene, and xylene. These solvents may be used singly or in combination of two or more types. The cyclic ethers are particularly preferred.

The reaction temperature during the condensation is generally 40 to 200° C. The reaction time is selected depending on the reaction temperature and is generally about 30 minutes to 50 hours.

The weight-average molecular weight of the polymer compound obtained in such a manner is generally 1,000 to 2,000,000, and preferably 2,000 to 1,000,000 as described above.

<Nonlinear Optical Compound>

The nonlinear optical compound used in the present invention is a π-conjugated compound that has an electron donative group at one end of a π-conjugated chain and an electron attractive group at the other end, and desirably has a larger molecular hyperpolarizability β. Examples of the electron donative group include a dialkylamino group, and examples of the electron attractive group include a cyano group, a nitro group, and a fluoroalkyl group.

Among these, as a nonlinear optical compound used in the present invention, a nonlinear optical compound having a tricyano-bonded furan ring is exemplified, and more specifically, a compound of formula (1) is preferable.

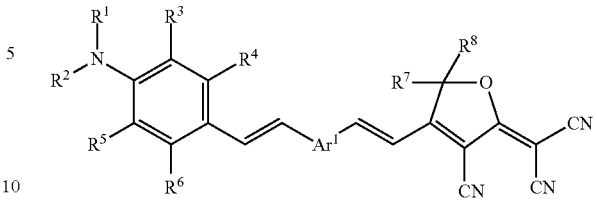

(1)

In formula (1), $R^1$ and $R^2$ are each independently a hydrogen atom, a $C_{1-10}$ alkyl group optionally having a substituent, or a $C_{6-10}$ aryl group.

The $C_{1-10}$ alkyl group herein may have a branched structure or a cyclic structure, and examples thereof include a methyl group, an ethyl group, an n-propyl group, an isopropyl group, a cyclopropyl group, an n-butyl group, an isobutyl group, a sec-butyl group, a tert-butyl group, an n-pentyl group, a neopentyl group, a cyclopentyl group, an n-hexyl group, a cyclohexyl group, an n-octyl group, an n-decyl group, a 1-adamantyl group, a benzyl group, and a phenethyl group.

Examples of the $C_{6-10}$ aryl group include a phenyl group, a tolyl group, a xylyl group, and a naphthyl group.

Examples of the substituent include an amino group; a hydroxy group; an alkoxycarbonyl group such as a methoxycarbonyl group and a tert-butoxycarbonyl group; a silyloxy group such as a trimethylsilyloxy group, a tert-butyldimethylsilyloxy group, a tert-butyldiphenylsilyloxy group, and a triphenylsilyloxy group; and a halogen atom.

In formula (1), $R^3$ to $R^6$ are each independently a hydrogen atom, a $C_{1-10}$ alkyl group, a hydroxy group, a $C_{1-10}$ alkoxy group, a $C_{2-11}$ alkylcarbonyloxy group, a $C_{6-10}$ aryloxy group, a $C_{7-11}$ arylcarbonyloxy group, a silyloxy group having a $C_{1-6}$ alkyl group and/or a phenyl group, or a halogen atom.

Examples of the $C_{1-10}$ alkyl group herein include the same groups as those recited above.

The $C_{1-10}$ alkoxy group may have a branched structure or a cyclic structure, and examples thereof include a methoxy group, an ethoxy group, an n-propoxy group, an isopropoxy group, a cyclopropoxy group, an n-butoxy group, an isobutoxy group, a sec-butoxy group, a tert-butoxy group, an n-pentyloxy group, a neopentyloxy group, a cyclopentyloxy group, an n-hexyloxy group, a cyclohexyloxy group, an n-octyloxy group, an n-decyloxy group, 1-adamantyloxy group, a benzyloxy group, and a phenetoxy group.

The $C_{2-11}$ alkylcarbonyloxy group may have a branched structure or a cyclic structure, and examples thereof include an acetoxy group, a propionyloxy group, a butyryloxy group, an isobutyryloxy group, a cyclopropanecarbonyloxy group, a pentanoyloxy group, a 2-methylbutanoyloxy group, a 3-methylbutanoyloxy group, a pivaloyloxy group, a hexanoyloxy group, a 3,3-dimethylbutanoyloxy group, a cyclopentanecarbonyloxy group, a heptanoyloxy group, a cyclohexancarbonyloxy group, an n-nonanoyloxy group, an n-undecanoyloxy group, 1-adamantanecarbonyloxy group, a phenylacetoxy group, and a 3-phenylpropanoyloxy group.

Examples of the $C_{6-10}$ aryloxy group include a phenoxy group, a naphthalene-2-yloxy group, a furan-3-yloxy group, and a thiophene-2-yloxy group.

Examples of the $C_{7-11}$ arylcarbonyloxy group include a benzoyloxy group, a 1-naphthoyloxy group, a furan-2-carbonyloxy group, and a thiophene-3-carbonyloxy group.

Examples of the silyloxy group having a $C_{1-6}$ alkyl group and/or a phenyl group include silyloxy groups such as a trimethylsilyloxy group, a tert-butyldimethylsilyloxy group, a tert-butyldiphenylsilyloxy group, and a triphenylsilyloxy group.

Examples of the halogen atom include the same atoms as those recited for the $R^{19}$ to $R^{52}$.

In formula (1), $R^7$ and $R^8$ are each independently a hydrogen atom, a $C_{1-5}$ alkyl group, a $C_{1-5}$ haloalkyl group, or a $C_{6-10}$ aryl group.

Examples of the $C_{1-5}$ alkyl group herein include the same groups as those recited for the $R^{19}$ to $R^{52}$.

Examples of the $C_{1-5}$ haloalkyl group include the same groups as those recited for the $R^{53}$ to $R^{76}$.

Examples of the $C_{6-10}$ aryl group include the same groups as those recited for the $R^1$ and $R^2$.

As specific combinations of the $R^7$ and $R^8$, methyl group-methyl group, methyl group-trifluoromethyl group, and trifluoromethyl group-phenyl group are preferred.

In formula (1), $Ar^1$ is a divalent organic group of formula ($Ar^1$-a) or formula ($Ar^1$-b):

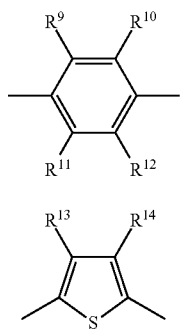

In the formulae, $R^9$ to $R^{14}$ are each independently a hydrogen atom, a $C_{1-10}$ alkyl group optionally having a substituent, or a $C_{6-10}$ aryl group.

Specific examples of the $C_{1-10}$ alkyl group, the $C_{6-10}$ aryl group, and the substituent include those exemplified above.

As a compound corresponding to the nonlinear optical compound used in the present invention, the following compound is reported as a nonlinear optical compound having a tricyano heterocyclic structure containing developed π-conjugated chains and very strong electron attractive groups and having an extremely large molecular hyperpolarizability β (Non-patent Document 1: Chem. Mater. 2001, 13, 3043-3050).

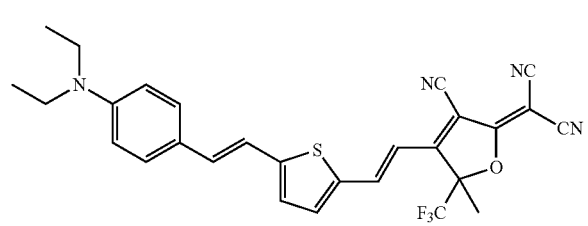 [SMILES: CCN(CC)c1ccc(/C=C/c2ccc(/C=C/C3=C(C#N)C(=C(C#N)C#N)OC3(C)C(F)(F)F)s2)cc1]

Furthermore, by converting a dialkylanilino moiety that is an electron donative group in the above structure into various structures, the molecular hyperpolarizability β can be made larger (Non-patent Document 2: J. Polym. Sci. Part A. 2011, Vol. 49, p47).

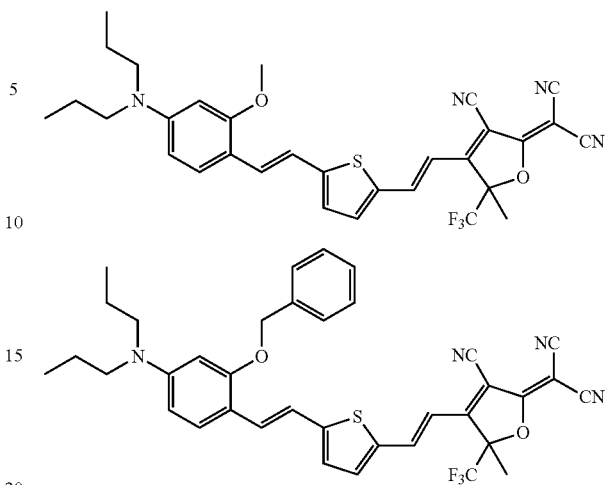

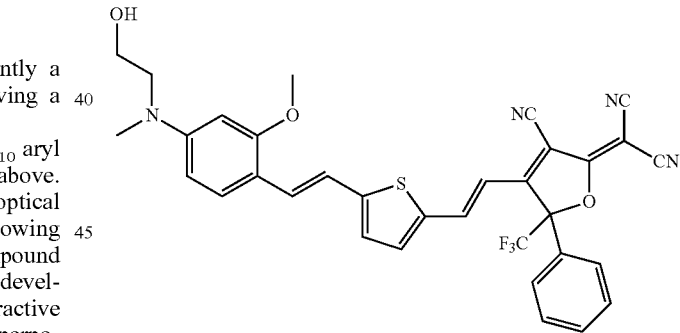

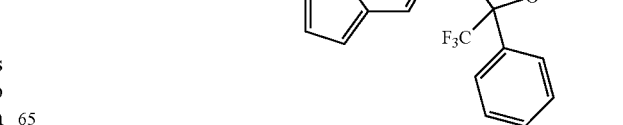

-continued

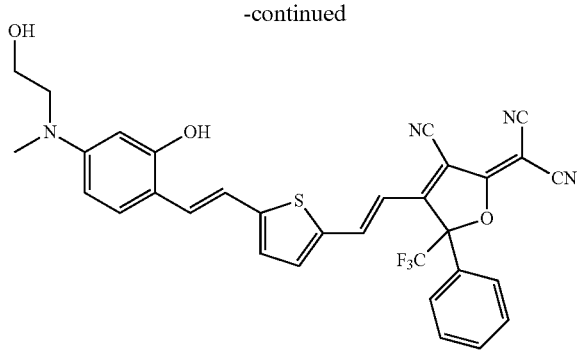

<Blend Ratio>

In the cladding material of the present invention, the blend ratio between the polymer compound including the triarylamine structure and the nonlinear optical compound is appropriately adjusted so that the resistance value is smaller than the resistance value of a core described later. The blending amount of the nonlinear optical compound is generally 0.1 to 50 parts by mass and more preferably 0.5 to 10 parts by mass with respect to 100 parts by mass of the polymer compound.

<Other Components that can be Blended>

Into the cladding material of the present invention, a cross-linking agent, a surfactant, a leveling agent, an antioxidant, a light stabilizer, or the like can be blended within a range not affecting the performance of the optical waveguide as a cladding material.

As the cross-linking agent, general-purpose products can be used, and isocyanates (including blocked isocyanate) are preferably used.

Examples of such general-purpose isocyanates include CORONATE (registered trademark) 2507, 2513, AP-Staple (manufactured by Nippon Polyurethane Industry Co., Ltd.); TAKENATE (registered trademark) B-882N, B-830, B-815N, B-842N, B-846N, B-870N, B-874N (manufactured by Mitsui Chemicals, Inc.); Burnock (registered trademark) D-500, D-550, B3-867 (manufactured by DIC Corporation); DURANATE (registered trademark) MF-B60X, MF-K60X (manufactured by Asahi Kasei Chemicals Corp.); and ELASTRON (registered trademark) BN-P17, BN-04, BN-08, BN-44, BN-45 (manufactured by Dai-ichi Kogyo Seiyaku Co., Ltd.).

These cross-linking agents may be used singly or in combination of two or more types.

[Optical Waveguide]

The optical waveguide of the present invention is an optical waveguide including a core and a cladding that surrounds the entire periphery of the core and has a refractive index smaller than that of the core, and is characterized in that the cladding is formed of the cladding material containing the polymer compound including the triarylamine structure and the nonlinear optical compound described above.

<Core>

In the optical waveguide of the present invention, the core only has to be formed of a material having a refractive index larger than the refractive index of the cladding formed.

For example, it is preferable that an organic nonlinear optical compound exhibiting a secondary nonlinear optical effect be contained in the core in a manner dispersing in a polymer matrix, or be contained in the core in a manner bound to a side chain of the polymer compound.

The organic nonlinear optical compound is preferably the nonlinear optical compound having the tricyano-bonded furan ring of formula (1).

When the nonlinear optical compound is dispersed in a polymer matrix, it is necessary to uniformly disperse the nonlinear optical compound at a high concentration in the matrix, and thus it is preferable that the polymer matrix exhibit high compatibility with the nonlinear optical compound. From the viewpoint of being used as the core of the optical waveguide, it is preferable that the polymer matrix have excellent transparency and formability.

Examples of such a polymer matrix material include resins such as poly(methyl methacrylate), polycarbonate, polystyrene, silicone-based resin, epoxy-based resin, polysulfone, polyethersulfone, and polyimide.

Examples of a method for dispersing in the polymer matrix include a method including dissolving a nonlinear optical compound and a matrix material at an appropriate ratio in organic solvent, applying this solution onto a substrate, and drying the solution to form a thin film.

When a nonlinear optical compound is bound to a side chain of a polymer compound, it is necessary for the side chain of the polymer compound to have a functional group that can form a covalent bond with the nonlinear optical compound. Examples of such a functional group include an isocyanate group, a hydroxy group, a carboxy group, an epoxy group, an amino group, a halogenated aryl group, and a halogenated acyl group.

These functional groups can form a covalent bond with, for example, a hydroxy group of the nonlinear optical compound having the tricyano-bonded furan ring of formula (1).

When the nonlinear optical compound is bound to a side chain of the polymer compound, to adjust the content of the nonlinear optical compound, the core may be formed so that a unit structure of the polymer matrix and a unit structure of the polymer compound to which the nonlinear polymer compound is bound copolymerize.

The blend ratio of the nonlinear optical compound in the core is appropriately adjusted because of the necessity of improving the electro-optical properties. The blending amount of the nonlinear optical compound is generally 1 to 1,000 parts by mass and more preferably 10 to 100 parts by mass with respect to 100 parts by mass of the polymer compound.

[Production Method of Optical Waveguide]

The optical waveguide of the present invention is produced by a method including: a step of forming a lower cladding using the cladding material described above; a step of forming on the lower cladding the core containing the nonlinear optical compound having the tricyano-bonded furan ring of formula (1) or the derivative thereof; and a step of forming an upper cladding on the core using the cladding material, in which the method includes, before and/or after the step of forming the upper cladding, a step of performing a polarization orientation process on the nonlinear optical compound or the derivative thereof contained in the core.

More specifically, in a case of producing a ridge-type optical waveguide, for example, the optical waveguide is produced through the following steps. In a case of producing a slab-type optical waveguide, step (3) is performed after step (1) without step (2) being performed.

(1) a step of forming a lower cladding using the cladding material;

(2) a step of forming a resist layer having photosensitivity to ultraviolet rays on the lower cladding, radiating ultraviolet light onto a surface of the resist layer through a photomask and carrying out development to form a core pattern, transferring the core pattern to the lower cladding using the core pattern as a mask, and removing the resist layer;
(3) a step of forming on the lower cladding a core containing the nonlinear optical compound having the tricyano-bonded furan ring of formula (1) or the derivative thereof; and
(4) a step of forming an upper cladding on the core using the cladding material.

Before and/or after step (4), the method further includes step (5) below.
(5) a step of performing a polarization orientation process on the nonlinear optical compound or the derivative thereof contained in the core.

The production method of the optical waveguide will be described in detail below.

<(1) Step of Forming Lower Cladding>

First, a thin film serving as a lower cladding is formed using the cladding material.

More specifically, a method is exemplified in which the cladding material is appropriately dissolved or dispersed in organic solvent to prepare a varnish (film forming material), the varnish is applied onto a suitable substrate by a coating method such as spin coating, blade coating, dip coating, roll coating, bar coating, die coating, an inkjet method, or a printing method (anastatic printing, intaglio printing, planographic printing, screen printing, etc.), and the solvent is dried. Among these coating methods, the spin coating is preferred. When the spin coating is used, coating can be completed within a short period of time. Accordingly, the spin coating can be used even for a highly volatile solution, and also, coating can be performed in a highly uniform manner. Thus, the spin coating is advantageous.

A method for drying the solvent is not particularly limited and, for example, the solvent could be vaporized by using a hot plate or an oven under suitable atmosphere, i.e., in the air, an inert gas such as nitrogen, a vacuum, or the like. This makes it possible to obtain a thin film having a uniform film formation surface. The drying temperature is not particularly limited as long as the solvent can be vaporized, but is preferably 40 to 250° C.

The organic solvent used for the film forming material herein is not particularly limited as long as the cladding material can be dissolved or dispersed.

Specific examples of such an organic solvent include aromatic hydrocarbons such as toluene, p-xylene, o-xylene, m-xylene, ethylbenzene, and styrene; aliphatic hydrocarbons such as n-hexane and n-heptane; halogenated hydrocarbons such as chlorobenzene, o-dichlorobenzene, chloroform, dichloromethane, dibromomethane, and 1,2-dichloroethane; ketones such as acetone, ethyl methyl ketone, isopropyl methyl ketone, isobutyl methyl ketone, butyl methyl ketone, diacetone alcohol, diethyl ketone, cyclopentanone, and cyclohexanone; esters such as ethyl acetate, propyl acetate, isopropyl acetate, butyl acetate, isobutyl acetate, ethyl lactate, and γ-butyrolactone; amides such as N,N-dimethylformamide, N,N-dimethylacetamide, N-methyl-2-pyrrolidone, and N-cyclohexyl-2-pyrrolidone; alcohols such as methanol, ethanol, propanol, isopropanol, allyl alcohol, butanol, isobutanol, tert-butanol, pentanol, 2-methyl butanol, 2-methyl-2-butanol, cyclohexanol, 2-methyl pentanol, octanol, 2-ethylhexanol, benzyl alcohol, furfuryl alcohol, and tetrahydrofurfuryl alcohol; glycols such as ethylene glycol, propylene glycol, hexylene glycol, trimethylene glycol, diethylene glycol, 1,3-butanediol, 1,4-butanediol, and 2,3-butanediol; ethers such as diethyl ether, diisopropyl ether, tetrahydrofuran, 1,4-dioxane, ethylene glycol dimethyl ether, diethylene glycol dimethyl ether, diethylene glycol diethyl ether, and triethylene glycol dimethyl ether; glycol ethers such as ethylene glycol monomethyl ether, ethylene glycol monoethyl ether, ethylene glycol monoisopropyl ether, ethylene glycol monobutyl ether, ethylene glycol monomethyl ether acetate, ethylene glycol monoethyl ether acetate, propylene glycol monomethyl ether, propylene glycol monoethyl ether, propylene glycol monobutyl ether, propylene glycol monomethyl ether acetate, butylene glycol monomethyl ether, diethylene glycol monomethyl ether, diethylene glycol monoethyl ether, diethylene glycol monoethyl ether acetate, dipropylene glycol monomethyl ether, and dipropylene glycol monoethyl ether; 1,3-dimethyl-2-imidazolidinone; and dimethyl sulfoxide. These organic solvents may be used singly or in combination of two or more types.

The substrate for forming the lower cladding is not particularly limited, but is preferably a substrate that is excellent in flatness. A metal substrate, a silicon substrate, and a transparent substrate are exemplified, and can be appropriately selected depending on the form of the optical waveguide. Preferred examples of the metal substrate include gold, silver, copper, platinum, aluminum, and chromium, and preferred examples of the transparent substrate include substrates such as glass and plastic (poly(ethylene terephthalate), etc.).

When a lower electrode is arranged between the substrate and the lower cladding, a known electrode can be used as the electrode. The lower electrode may be a metal-evaporation layer or a transparent electrode layer. Preferred examples of the metal evaporated include gold, silver, copper, platinum, aluminum, and chromium. Preferred examples of the transparent electrode layer include indium tin oxide (ITO), fluorine-doped tin oxide (FTO), and antimony-doped tin oxide.

<(2) Step of Transferring Core Pattern>

Subsequently, a resist layer having photosensitivity to ultraviolet rays is formed on the lower cladding, and a mask pattern of the core is formed by a photolithographic method in which ultraviolet light is radiated onto a surface of the resist layer through a photomask and development is carried out.

A material of the resist layer is not particularly limited as long as it is a material that can be exposed to light to develop a fine pattern by the photolithographic method and with which a solvent used at this step does not elute the lower cladding, but is preferably made of a positive or negative photoresist material. Examples of a light source used for the pattern formation include a mercury lamp, a KrF laser, and an ArF laser.

Subsequently, dry etching using gas is performed with the mask pattern of the core of the resist layer used as a mask, whereby the core pattern is transferred onto the lower cladding. A reactive ion etching using a gas such as $CHF_3$, $O_2$, Ar, or $CF_4$ in general, which is appropriately selected based on etching characteristics of the resist and the lower cladding is preferably used for this dry etching.

After the dry etching, the resist layer used as the mask is removed with a solvent.

<(3) Step of Forming Core>

Subsequently, on the lower cladding on which the core pattern is formed, the core containing the nonlinear optical compound having the tricyano-bonded furan ring of formula (1) or the derivative thereof.

Specific examples therefore include, as described in <Core> above, a method in which the nonlinear optical compound having the tricyano-bonded furan ring of formula (1) and the polymer matrix material are dissolved in a suitable organic solvent at an appropriate ratio to prepare a varnish, and the varnish is applied onto a substrate and dried to form a thin film, and a method in which a polymer compound having at a side chain a derivative of the nonlinear optical compound having the tricyano-bonded furan ring of formula (1) is dissolved in a suitable organic solvent to prepare a varnish, and the varnish is applied onto a substrate and dried to form a thin film.

As the coating method and the drying condition of the varnish and the organic solvent herein, those recited in <(1) Step of Forming Lower Cladding> can be used.

As the organic solvent, an organic solvent that does not dissolve the lower cladding needs to be selected so as not to dissolve the lower cladding during the core formation.

<(4) Step of Forming Upper Cladding>

Using the cladding material, a thin film serving as the upper cladding is formed in the same manner as in <(1) Step of Forming Lower Cladding>.

<(5) Step of Performing Polarization Orientation Process>

Before and/or after the step of forming the upper cladding, the polarization orientation process is performed by an electric field poling method for applying an electric field to the nonlinear optical compound contained in the core. The polarization orientation process is performed near the glass transition temperature of the core or higher, and the polarization of the nonlinear optical compound is oriented by the electric field application in the direction of the electric field application. The orientation is then maintained even after the temperature is cooled down to room temperature, whereby electro-optical properties can be imparted to the core and the optical waveguide.

A method of applying a direct voltage between electrodes arranged at the top and the bottom of a layered structure or a method using corona discharge to the surface of core is used for the electric field application. From the view point of easiness of the orientation process and uniformity, the process of applying the electric field with the electrodes is preferred.

EXAMPLES

The present invention will be described in further detail with reference to examples below but is not limited to the examples.

In the examples, apparatuses and conditions used for preparation of specimens and analysis of physical properties are as follows.

(1) GPC (Gel Permeation Chromatography)
 Apparatus: HLC-8220GPC manufactured by Tosoh Corporation
 Column: KF-804L+KF-805L manufactured by Showa Denko K. K.
 Column temperature: 40° C.
 Solvent: Tetrahydrofuran (THF)
 Detector: RI
(2) $^1$H NMR Spectrum
 Apparatus: JNM-ECA700 manufactured by JEOL Ltd.
 Solvent: CDCl$_3$
 Internal standard: Tetramethylsilane
(3) Differential Scanning Calorimeter
 Apparatus: DSC 204F1 Phoenix (registered trademark) manufactured by NETZSCH
 Temperature elevation rate: 30° C./min
 Measurement temperature: 25 to 300° C.
(4) Spin Coater
 Apparatus: MS-A100 manufactured by Mikasa Co., Ltd.
(5) Hot Plate
 Apparatus: ND-2 manufactured by AS ONE Corporation
(6) Refractive Index
 Apparatus: Variable angle spectral ellipsometer VASE manufactured by J. A. Woollam Japan
(7) Resistivity
 Power-supply apparatus: HSA4052 manufactured by NF Corporation
 Measuring apparatus: 8340A digital ultra-high resistance/micro-current meter manufactured by ADC Corporation Example 1

Synthesis of Polymer Compound (1) Having Triarylamine Structure

Under a nitrogen atmosphere, 8.52 g (34.7 mmol) of triphenylamine [manufactured by Tokyo Chemical Industry Co., Ltd.], 11.54 g (69.5 mmol) of 4-(2-hydroxyethoxy) benzaldehyde [manufactured by Tokyo Chemical Industry Co., Ltd.], and 1.32 g (6.95 mmol) of p-toluenesulfonic acid monohydrate [manufactured by Junsei Chemical Co., Ltd.] were put in a 100-mL reaction flask, and 20 g of 1,4-dioxane was added and dissolved therein. This solution was heated up to 85° C., and was stirred to start polymerization. After the reaction was performed for 5 hours and 30 minutes, the solution was cooled down to room temperature, and was stirred with 60 g of tetrahydrofuran and 4.72 g (77.7 mmol) of a 28% by mass ammonia aqueous solution added. This reaction solution was added dropwise into 500 g of methanol, and was subjected to reprecipitation. A light-yellow solid thus precipitated was vacuum dried, and then was dissolved in 67 g of tetrahydrofuran. The solution was added dropwise into a mixed solution of 4.72 g of a 28% by mass ammonia aqueous solution, 450 g of methanol, and 50 g of ion-exchange water, and was subjected to reprecipitation. A colorless solid thus obtained was dried, and 6.88 g of a polymer compound (1) having a repeating unit of formula [A] below was obtained. The weight-average molecular weight Mw of this polymer compound (1) measured in terms of polystyrene by GPC was 32,800, and the degree of distribution Mw (weight-average molecular weight)/Mn (number-average molecular weight) was 3.70.

[A]

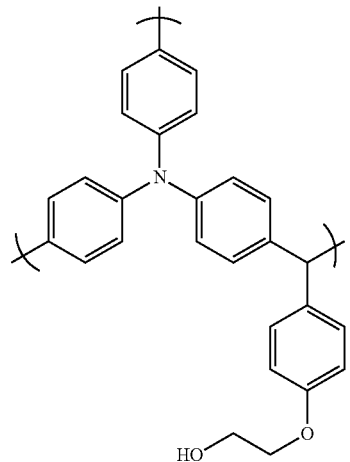

Example 2

Synthesis of Polymer Compound (2) Having Triarylamine Structure

Under a nitrogen atmosphere, 10.0 g (40.8 mmol) of triphenylamine [manufactured by Tokyo Chemical Industry Co., Ltd.], 13.6 g (81.5 mmol) of 3-(2-hydroxyethoxy) benzaldehyde [manufactured by Tokyo Chemical Industry Co., Ltd.], and 0.78 g (4.08 mmol) of p-toluenesulfonic acid monohydrate [manufactured by Junsei Chemical Co., Ltd.] were put in a 100-mL reaction flask, and 24 g of 1,4-dioxane was added and dissolved therein. This solution was heated up to 85° C., and was stirred to start polymerization. After the reaction was performed for 3 hours and 30 minutes, the solution was cooled down to room temperature, and was stirred with 70 g of tetrahydrofuran and 9.90 g (163 mmol) of a 28% by mass ammonia aqueous solution added. This reaction solution was added dropwise into 510 g of methanol, and was subjected to reprecipitation. A light-yellow solid thus precipitated was vacuum dried, and then was dissolved in 60 g of tetrahydrofuran. This solution was added dropwise into a mixed solution of 9.90 g of a 28% by mass ammonia aqueous solution, 450 g of methanol, and 50 g of ion-exchange water, and was subjected to reprecipitation. A colorless solid thus obtained was dried, and 7.90 g of a polymer compound (2) having a repeating unit of formula [B] below was obtained. The weight-average molecular weight Mw of this polymer compound (2) measured in terms of polystyrene by GPC was 17,000, and the degree of distribution Mw/Mn was 2.54.

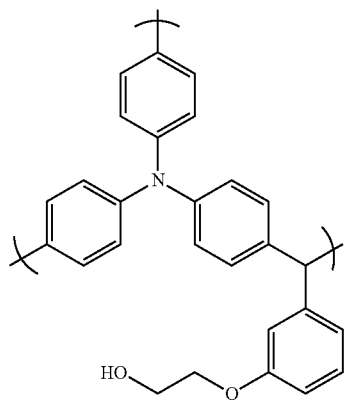

[B]

Example 3

Synthesis of Polymer Compound (3) Having Triarylamine Structure

Under a nitrogen atmosphere, 3.00 g (16.4 mmol) of diphenylmethylamine [manufactured by Tokyo Chemical Industry Co., Ltd.], 2.01 g (8.19 mmol) of triphenylamine [manufactured by Tokyo Chemical Industry Co., Ltd.], 8.16 g (49.11 mmol) of 4-(2-hydroxyethoxy)benzaldehyde [manufactured by Tokyo Chemical Industry Co., Ltd.], and 0.47 g (2.46 mmol) of p-toluenesulfonic acid monohydrate [manufactured by Junsei Chemical Co., Ltd.] were put in a 100-mL reaction flask, and 13 g of 1,4-dioxane was added and dissolved therein. This solution was heated up to 85° C., and was stirred to start polymerization. After the reaction was performed for 3 hours and 30 minutes, the solution was cooled down to room temperature, and was stirred with 63 g of tetrahydrofuran and 1.49 g (24.5 mmol) of a 28% by mass ammonia aqueous solution added. This reaction solution was added dropwise into 400 g of methanol, and was subjected to reprecipitation. A light-yellow solid thus precipitated was vacuum dried, and then was dissolved in 63 g of tetrahydrofuran. This solution was added dropwise into a mixed solution of 1.49 g of a 28% by mass ammonia aqueous solution, 400 g of methanol, and 100 g of ion-exchange water, and was subjected to reprecipitation. A colorless solid thus obtained was dried, and 5.58 g of a polymer compound (3) having two types of repeating units of formula [C] below was obtained. The weight-average molecular weight Mw of this polymer compound (3) measured in terms of polystyrene by GPC was 12,600, and the degree of distribution Mw/Mn was 2.10.

[C]

Example 4

Synthesis of Polymer Compound (4) Having Triarylamine Structure

Under a nitrogen atmosphere, 9.00 g (49.1 mmol) of diphenylmethylamine [manufactured by Tokyo Chemical Industry Co., Ltd.], 6.02 g (24.6 mmol) of triphenylamine [manufactured by Tokyo Chemical Industry Co., Ltd.], 24.5 g (147 mmol) of 3-(2-hydroxyethoxy)benzaldehyde [manufactured by Tokyo Chemical Industry Co., Ltd.], and 1.40 g (7.37 mmol) of p-toluenesulfonic acid monohydrate [manufactured by Junsei Chemical Co., Ltd.] were put in a 100-mL reaction flask, and 39.5 g of 1,4-dioxane was added and dissolved therein. This solution was heated up to 85° C., and was stirred to start polymerization. After the reaction was performed for 70 minutes, the solution was cooled down to room temperature, and was stirred with 120 g of tetrahydrofuran and 8.95 g (147 mmol) of a 28% by mass ammonia aqueous solution added. This reaction solution was added dropwise into 560 g of methanol, and was subjected to reprecipitation. A light-yellow solid thus precipitated was vacuum dried, and then was dissolved in 220 g of tetrahydrofuran. This solution was added dropwise into a mixed solution of 8.95 g of a 28% by mass ammonia aqueous solution, 400 g of methanol, and 200 g of ion-exchange water, and was subjected to reprecipitation. A colorless solid thus obtained was dried, and 17.6 g of a polymer compound (4) having two types of repeating units of formula [D] below was obtained. The weight-average molecular weight Mw of this polymer compound (4) measured in terms of polystyrene by GPC was 28,000, and the degree of distribution Mw/Mn was 4.14.

tetrahydrofuran added. This solution was then added dropwise into 930 g methanol, and was subjected to reprecipitation. A light-yellow solid thus obtained was collected by filtration, and was dissolved again in 140 g of tetrahydrofuran. This solution was added dropwise into 900 g of methanol, and was subjected to reprecipitation. A light-yellow solid thus obtained was vacuum dried at 40° C. for 6 hours, and 23.4 g of a polymer compound (5) having two types of repeating units of formula [E] below was obtained. The weight-average molecular weight Mw of this polymer compound (5) measured in terms of polystyrene by GPC was 22,400, and the degree of distribution Mw/Mn was 3.18.

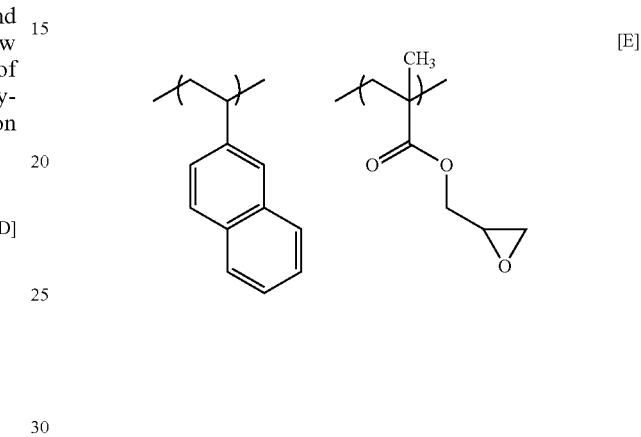

[E]

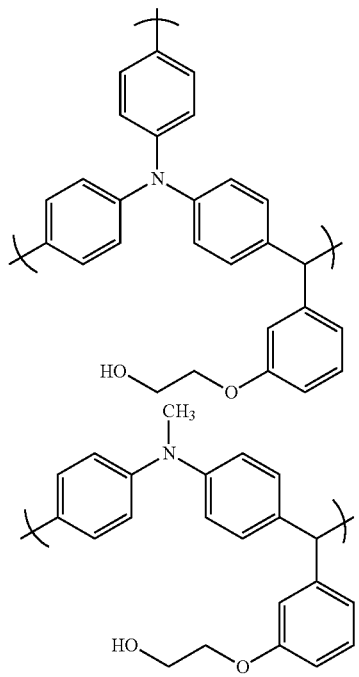

[D]

Comparative Synthesis Example 1

Synthesis of Polymer Compound (5) Having No Triarylamine Structure 37.0 g (0.240 mol) of vinylnaphthalene [manufactured by New Nippon Steel Chemical Co., Ltd.] and 8.53 g (0.060 mol) of glycidyl methacrylate [manufactured by Tokyo Chemical Industry Co., Ltd.] were put in a 300-mL reaction flask equipped with a reflux column, and 68 g of dimethylacetamide was added and dissolved therein. 1.11 g (4.80 mmol) of dimethyl 2,2'-azobisisobutyrate [manufactured by Wako Pure Chemical Industries, Ltd.] was added to the resultant solution, and the inside of the flask was subjected to nitrogen substitution. This solution was stirred at 70° C. for 8 hours, and was allowed to sit to cool down to room temperature. This reaction solution was diluted with 43 g of Comparative Synthesis Example 2

Synthesis of Polymer Compound (6) Having Triarylamine Structure and Having No Cross-Linking Moiety Under a nitrogen atmosphere, 2.00 g (10.9 mmol) of diphenylmethylamine [manufactured by Tokyo Chemical Industry Co., Ltd.], 1.34 g (5.46 mmol) of triphenylamine [manufactured by Tokyo Chemical Industry Co., Ltd.], 3.47 g (32.7 mmol) of benzaldehyde [manufactured by Tokyo Chemical Industry Co., Ltd.], and 0.31 g (1.64 mmol) of p-toluenesulfonic acid monohydrate [manufactured by Junsei Chemical Co., Ltd.] were put in a 50-mL reaction flask, and 7 g of 1,4-dioxane was added and dissolved therein. This solution was heated up to 85° C., and was stirred to start polymerization. After the reaction was performed for 3 hours, the solution was cooled down to room temperature, and was stirred with 60 g of tetrahydrofuran and 2.98 g (49.2 mmol) of a 28% by mass ammonia aqueous solution added. This reaction solution was added dropwise into 440 g of methanol, and was subjected to reprecipitation. A light-yellow solid thus precipitated was vacuum dried, and then was dissolved in 60 g of THF. This solution was added dropwise into a mixed solution of 2.98 g of a 28% by mass ammonia aqueous solution, 400 g of methanol, and 100 g of ion-exchange water, and was subjected to reprecipitation. A colorless solid thus obtained was dried, and 2.96 g of a polymer compound (6) having two types of repeating units of formula [F] below was obtained. The weight-average molecular weight Mw of this polymer compound (6) measured in terms of polystyrene by GPC was 63,000, and the degree of distribution Mw/Mn was 9.34.

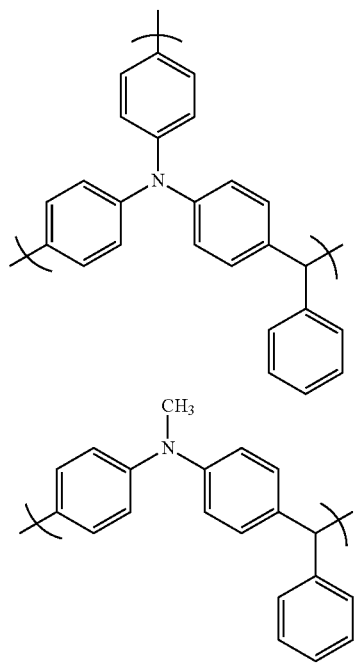

Synthesis Example 1

Synthesis of Nonlinear Optical Compound

As a nonlinear optical compound having a tricyano-bonded furan ring, a compound of Formula [G] below was used. This compound was synthesized according to a method disclosed in Tetrahedron. lett., 51, p5823 (2010) by X. Zhang, et al.

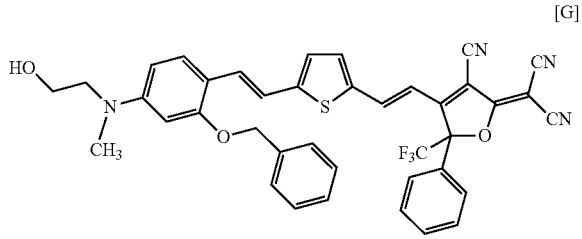 [SMILES: CN(CCO)c1ccc(/C=C/c2ccc(/C=C/C3=C(C#N)C(=C(C#N)C#N)OC3(c3ccccc3)C(F)(F)F)s2)c(OCc2ccccc2)c1]

Example 5

Crack Resistance of Polymer Compound Having Triarylamine Structure

The polymer compound (1) obtained in Example 1 was dissolved in cyclohexanone so that the content was 20% by mass, and 2,4-tolylenediisocyanate [manufactured by Tokyo Chemical Industry Co., Ltd.] was added therein so that the content was 10% by mass with respect to the polymer compound (1). A film was formed on a glass substrate by spin coating, and was subjected to heat treatment at 150° C. for 10 minutes to be cured. The film thickness of the film thus obtained was 2.39 μm. As a result of microscopic observation, it was observed that a uniform film having no crack was obtained.

Example 6

The polymer compound (2) obtained in Example 2 was dissolved in cyclohexanone so that the content was 20% by mass, and 2,4-tolylenediisocyanate [manufactured by Tokyo Chemical Industry Co., Ltd.] was added therein so that the content was 10% by mass with respect to the polymer compound (2). A film was formed on a glass substrate by spin coating, and was subjected to heat treatment at 150° C. for 10 minutes to be cured. The film thickness of the film thus obtained was 3.00 μm. As a result of microscopic observation, it was observed that a uniform film having no crack was obtained.

Example 7

The polymer compound (3) obtained in Example 3 was dissolved in cyclohexanone so that the content was 20% by mass. With this solution, a film was formed on a glass substrate by spin coating, and was dried at 150° C. for 10 minutes. The film thickness of the film thus obtained was 2.51 μm. As a result of microscopic observation, it was observed that a uniform film having no crack was obtained.

Example 8

The polymer compound (4) obtained in Example 4 was dissolved in cyclohexanone so that the content was 20% by mass. With this solution, a film was formed on a glass substrate by spin coating, and was dried at 150° C. for 10 minutes. The film thickness of the film thus obtained was 2.28 μm. As a result of microscopic observation, it was observed that a uniform film having no crack was obtained.

Comparative Example 1

The polymer compound (5) obtained in Comparative Synthesis Example 1 was dissolved in propylene glycol monomethyl ether acetate so that the content was 30% by mass. With this solution, a film was formed on a glass substrate by spin coating, and was dried at 150° C. for 10 minutes. The film thickness of the film thus obtained was 4.81 μm. As a result of microscopic observation, generation of a crack was observed.

Comparative Example 2

The polymer compound (6) obtained in Comparative Synthesis Example 2 was dissolved in cyclohexanone so that the content was 20% by mass. With this solution, a film was formed on a glass substrate by spin coating, and was dried at 150° C. for 10 minutes. The film thickness of the film thus obtained was 2.37 μm. As a result of microscopic observation, generation of a crack was observed.

<Refractive Index Measurement of High Molecule Compound Having Triarylamine Structure>

The polymer compounds (1) to (6) were dissolved in cyclohexanone so that the content was 10% by mass. With these solutions, films were formed on silicon substrates by spin coating, and were dried at 150° C. for 10 minutes. The refractive indices at 633 nm of the obtained films were measured by spectroscopic ellipsometry. The results obtained are shown in Table 1.

TABLE 1

Crack Resistance and Refractive Index of High Molecule Compound Having Triarylamine Structure

| | Polymer compound | Presence/absence of crack generated | Refractive index @ 633 nm |
|---|---|---|---|
| Example 5 | Compound (1) | Absent | 1.680 |
| Example 6 | Compound (2) | Absent | 1.674 |
| Example 7 | Compound (3) | Absent | 1.659 |
| Example 8 | Compound (4) | Absent | 1.665 |
| Comparative Example 1 | Compound (5) | Present | 1.634 |
| Comparative Example 2 | Compound (6) | Present | 1.667 |

Example 9

Measurement of Resistance Value of Cladding Material 0.51 g of the polymer compound (1) having the triarylamine structure obtained in Example 1 and 0.06 g of blocked isocyanate [DURANATE (registered trademark) MF-K60X manufactured by Asahi Kasei Chemicals Corp.] were dissolved in 2.4 g of cyclopentanone. Into this solution, 0.03 g of the nonlinear optical compound synthesized in Synthesis Example 1 was mixed and stirred. This solution was filtered with a filter having a pore diameter of 0.20 and then the filtrate was spin-coated on an ITO glass substrate (film thickness of 150 nm, surface resistance of 10Ω/□, manufactured by Sanyo Vacuum Industries Co., Ltd.). Subsequently, heating was performed with a hot plate at 150° C. for 30 minutes to perform drying and cross-linking. The film thickness of a cured film thus obtained was 1.7 μm. On this film, a film of gold having a thickness of 100 nm was formed as an upper electrode by sputtering to prepare a resistance measurement sample (1).

Comparative Example 3

A resistance measurement sample (2) was also prepared by the same operation as in Example 9 except that the nonlinear optical compound was not blended. The film thickness of a cured film obtained was 1.7 μm.

Each of the resistance measurement samples was placed on a heater, voltage of 120 V was applied thereto each at 20° C. and 130° C., and the current value was measured to calculate the resistivity. The results obtained are shown in Table 2.

As indicated in Table 2, the addition of the nonlinear optical compound significantly reduced the resistivity both at 20° C. and 130° C.

TABLE 2

Resistivity When Nonlinear Optical Compound Was Added to Cladding

| | Measurement sample | Introduction amount of nonlinear optical compound (% by mass (solid phase)) | Temperature (° C.) | Applied voltage (V) | Resistivity (Ω · m) |
|---|---|---|---|---|---|
| Example 9 | (1) | 6 | 20 | 120 | $2.0 \times 10^7$ |
| | | 6 | 130 | 120 | $2.0 \times 10^4$ |
| Comparative Example 3 | (2) | 0 | 20 | 120 | $1.5 \times 10^{14}$ |
| | | 0 | 130 | 120 | $1.7 \times 10^{11}$ |

<Measurement of Electro-Optical Constant>

To confirm the effect of reduction of the resistivity of cladding on the electric field orientation process of a core, a core having electro-optical properties was placed on the cladding, and was subjected to the electric field orientation process, and the electro-optical constant was measured.

Synthesis Example 2

Synthesis of Core Material

For the core, a polymer having repeating units of formula [H] below in which a nonlinear optical compound having a tricyano-bonded furan ring is bound to a side chain of the polymer compound was used. This polymer was synthesized according to a method disclosed in J. Polym. Sci. A, 49, p47 (2011) by X. Piao, et al. The ratio of the nonlinear optical compound (R portion in formula [H] below) in the polymer determined from the UV-Vis spectrum of the polymer obtained was 40% by mass.

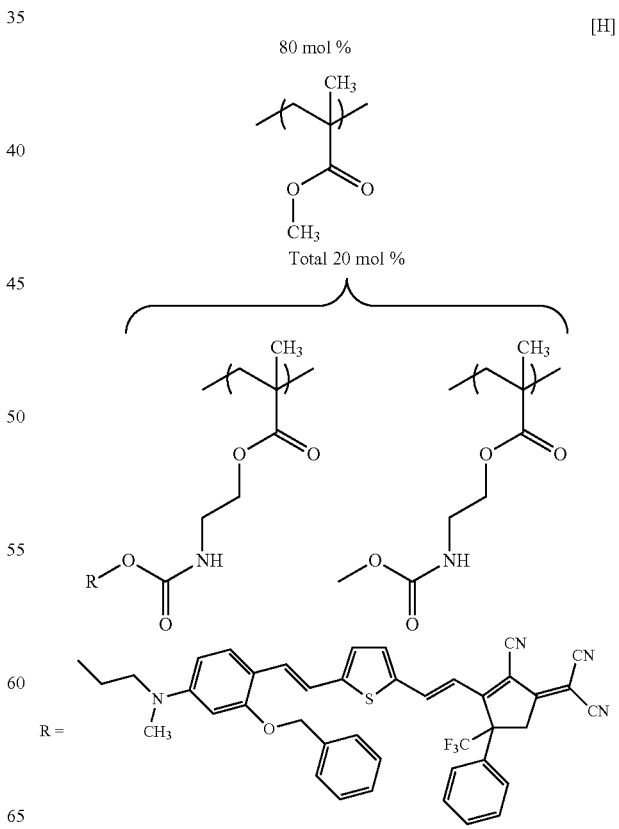

[H]

When the resistivity of the core formed of the polymer having the repeating units of formula [H] was measured in the same manner as in <Measurement of Resistivity of Cladding Material> above, the results were $3.5 \times 10^{11}$ [Ω·m] (20° C., 100V) and $2.7 \times 10^{9}$ [Ω·m] (130° C., 100V). In other words, the resistivity of the core was higher than the resistivity of the cladding indicated in Example 9, and thus it is expected that the voltage application to the core in the electric field orientation process can be efficiently performed.

Example 10

Production of Cladding/Core Layered Film 0.51 g of the polymer compound (1) having the triarylamine structure obtained in Example 1 and 0.06 g of blocked isocyanate [DURANATE (registered trademark) MF-K60X manufactured by Asahi Kasei Chemicals Corp.] were dissolved in 2.4 g of cyclopentanone. Into this solution, 0.03 g of the nonlinear optical compound synthesized in Synthesis Example 1 was mixed and stirred. This solution was filtered with a filter having a pore diameter of 0.20 μm, and then the filtrate was spin-coated on an ITO glass substrate. Subsequently, heating was performed with a hot plate at 150° C. for 30 minutes to perform drying and cross-linking, whereby a cladding was obtained.

0.45 g of the polymer having the repeating units of formula [H] obtained in Synthesis Example 2 was dissolved in 2.6 g of cyclopentanone, and this solution was spin-coated on the cladding, and dried at 80° C. for 6 hours under reduced pressure to prepare a core.

On the core, a film of gold having a thickness of 100 nm was formed as an upper electrode by sputtering.

The electro-optical constant of this cladding/core layered film was measured with a semiconductor laser having a wavelength of 1.31 μm used as a light source according to methods described in Appl. Phys. Lett. 56, p1734 (1990) by C. C. Teng, et al. and J. Appl. Phys. 77, p4632 (1995) by Y. Shuto, et al. More specifically, a specimen was placed on a heater and heated up to 130° C. near the glass transition temperature of the core, and then, while the electric field orientation process was being performed with a voltage up to 300 V applied between the electrodes, the electro-optical constant was measured. When the electro-optical constant reached the maximum value, the temperature was lowered to room temperature (about 25° C.), and then the voltage application was stopped. The measured value when it became stable was defined as the electro-optical constant of the specimen. The result obtained is given in Table 3.

In the table, r1 is an actually measured electro-optical constant obtained with the cladding/core layered structure, and r2 is an electro-optical constant calculated on the assumption that all modulation voltage is applied to the core formed of the polymer having the repeating units of formula [H] in consideration of the thickness of the cladding containing the nonlinear optical compound and the polymer compound (1) having the triarylamine structure.

The polymer having the repeating units of formula [H] used herein alone exhibits an electro-optical constant of 100 pm/V. Thus, from the result (r2=94 pm/V) shown in Table 3, it is found that the voltage is efficiently applied to the core also in the layered structure by using the cladding into which the nonlinear optical compound is introduced.

TABLE 3

Measurement of Electro-Optical Constant in Cladding/Core Layered Structure

| | Introduction amount of nonlinear optical compound* (% by mass (solid phase)) | Film thickness (μm) | | Applied voltage (V) | r1 (pm/V) | r2 (pm/V) |
|---|---|---|---|---|---|---|
| | | Core | Cladding | | | |
| Example 10 | 6 | 1.7 | 1.7 | 300 | 47 | 94 |

*The introduction amount of the nonlinear optical compound into the cladding

<Production of Ridge-Type Optical Waveguide>

By a production process illustrated in FIG. 1, a ridge-type optical waveguide element was prepared.

To begin with, a film was formed with a chrome layer of 5 nm followed by a gold layer of 100 nm on a silicon substrate 1 by vacuum deposition, which was a lower electrode 2 (FIG. 1(a)).

On the lower electrode 2, a lower cladding 3 was formed with a material used for forming a cladding in <Measurement of Electro-Optical Constant> above. More specifically, 0.51 g of the polymer compound (1) having the triarylamine structure obtained in Example 1 and 0.06 g of blocked isocyanate [DURANATE (registered trademark) MF-K60X manufactured by Asahi Kasei Chemicals Corp.] were dissolved in 2.4 g of cyclopentanone. Into this solution, 0.03 g of the nonlinear optical compound synthesized in Synthesis Example 1 was mixed and stirred. This solution was filtered with a filter having a pore diameter of 0.20 μm, and then the filtrate was spin-coated on the lower electrode 2. Subsequently, heating was performed with a hot plate at 150° C. for 30 minutes to perform drying and cross-linking, whereby the lower cladding 3 was formed (FIG. 1(a)).

On the cladding 3, a film of a photoresist 4 [ZPN1150-90 manufactured by Nippon ZEON Co., Ltd.] was formed (FIG. 1(b)), and was exposed to light through a linear mask of 4 μm wide and developed, whereby a ridge-type waveguide pattern was formed (FIG. 1(c)).

With this resist pattern used as a mask, the pattern was transferred onto the lower cladding 3 by reactive ion etching using $CHF_3$ gas. The height of the ridge herein (indicated by H in the drawing) was about 500 nm (FIG. 1(d)).

After the photoresist was removed by a photoresist solvent (acetone/ethanol mixed solvent) (FIG. 1(e)), a core 5 was formed on the lower cladding 3 by using a material used for forming the core in <Measurement of Electro-Optical Constant> above. More specifically, the lower cladding 3 was spin-coated with a solution prepared by dissolving 0.45 g of the polymer having the repeating units of [H] obtained in Synthesis Example 2 in 2.6 g of cyclopentanone, and was dried at 80° C. for 6 hours under reduced pressure to form the core 5 (FIG. 1(f)).

Furthermore, with the same material and by the same method as those for the lower cladding 3, an upper cladding 6 was formed on the core 5 (FIG. 1(g)).

Gold was then vacuum-deposited on the upper cladding 6 to form an upper electrode 7 (FIG. 1(h)).

In the end, the silicon substrate was cleaved along the crystal plane to form an end surface through which light enters or exits, which was used as a ridge-type optical waveguide.

Figure 2:
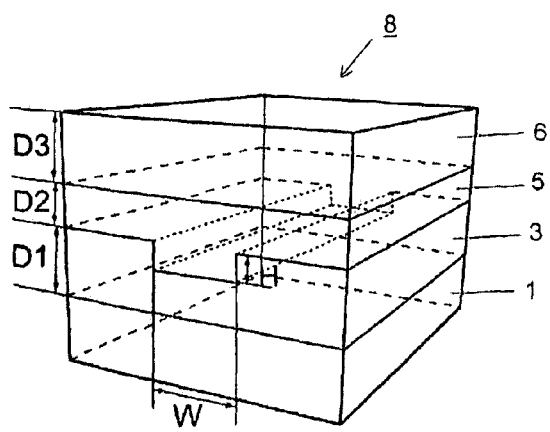
FIG. 2 is a diagram illustrating a conceptual diagram of a shape of the ridge-type optical waveguide produced in Examples.

FIG. 2 illustrates the shape of an optical waveguide 8 (core/cladding) thus prepared. In FIG. 2, the lower electrode 2 and the upper electrode 7 are omitted.

In FIG. 2, D1, D2, and D3 are the thickness of the lower cladding, the thickness of the core, and the thickness of the upper cladding, respectively; H is the height of the ridge portion; and W is the width of the waveguide.

DESCRIPTION OF THE REFERENCE NUMERALS

1 . . . substrate, 2 . . . lower electrode, 3 . . . lower cladding, 4 . . . photoresist, 5 . . . core, 6 . . . upper cladding, 7 . . . upper electrode, 8 . . . optical waveguide, D1 . . . thickness of lower cladding, D2 . . . thickness of core, D3 . . . thickness of upper cladding, H . . . height of ridge portion, W . . . width of waveguide

The invention claimed is:

1. A cladding material of an optical waveguide, comprising:
a polymer compound including a triarylamine structure; and
a nonlinear optical compound, wherein
the polymer compound including the triarylamine structure has a repeating unit of formula (2) or formula (3):

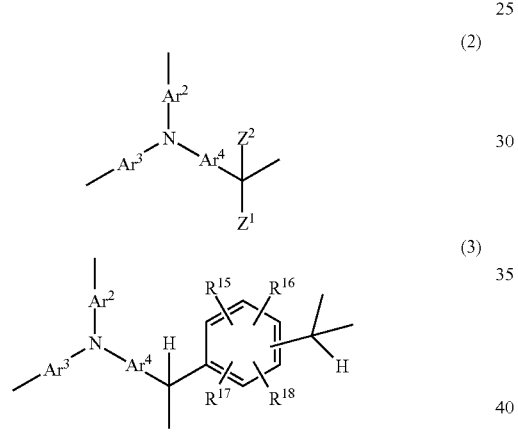

in formula (2) and formula (3), $Ar^2$ to $Ar^4$ are each independently any one of divalent organic groups of formula (4) to (8) below; in formula (2), $Z^1$ is a monovalent organic group of formula (9) below, and $Z^2$ is a hydrogen atom; and in formula (3), $R^{15}$ to $R^{18}$ are each independently a hydrogen atom (provided that $R^{15}$ and $R^{18}$ are not simultaneously hydrogen atoms), or a $C_{1-5}$ hydroxyalkyl group,

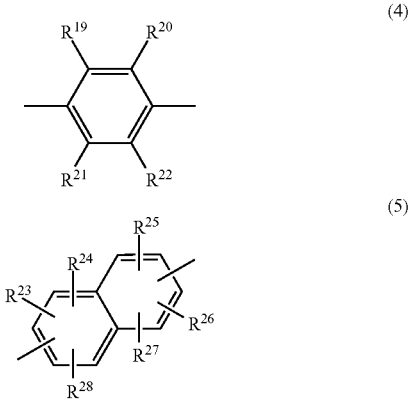

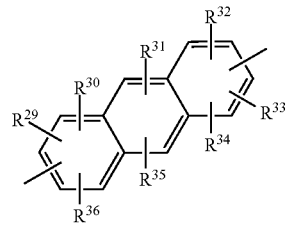

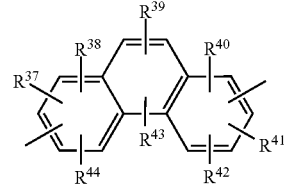

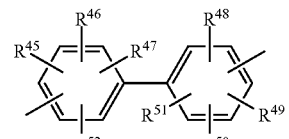

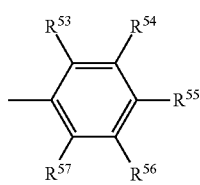

in the formulas, $R^{19}$ to $R^{52}$ are each independently a hydrogen atom, a $C_{1-5}$ alkyl group, an epoxy group, a carboxy group, a hydroxy group, a $C_{1-5}$ alkoxy group, or a halogen atom, in the formula, $R^{53}$ to $R^{57}$ are each independently a hydrogen atom (provided that $R^{53}$ to $R^{57}$ are not simultaneously hydrogen atoms), a $C_{1-5}$ hydroxyalkyl group, an $OR^{77}$ group, a $COR^{77}$ group, a $COOR^{77}$ group, or an $NR^{77}R^{78}$ group (in these formulae, $R^{77}$ is a $C_{1-5}$ hydroxyalkyl group and $R^{78}$ is a hydrogen atom).

2. The cladding material according to claim 1, wherein the nonlinear optical compound is a compound having a tricyano-bonded furan ring.

3. The cladding material according to claim 2, wherein the compound having the tricyano-bonded furan ring is a compound of formula (1):

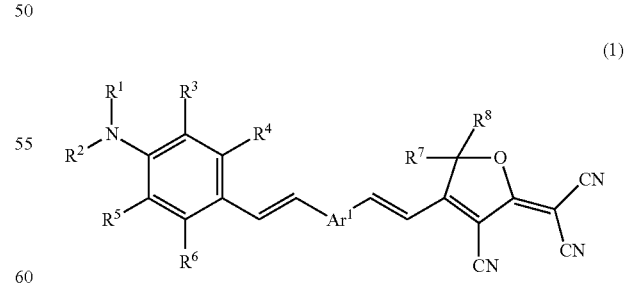

in the formula, $R^1$ and $R^2$ are each independently a hydrogen atom, a $C_{1-10}$ alkyl group optionally having a substituent, or a $C_{6-10}$ aryl group; $R^3$ to $R^6$ are each independently a hydrogen atom, a $C_{1-10}$ alkyl group, a hydroxy group, a $C_{1-10}$ alkoxy group, a $C_{2-11}$ alkylcarbonyloxy group, a $C_{6-10}$ aryloxy group, a $C_{7-11}$ arylcarbonyloxy group, a silyloxy group having a $C_{1-6}$ alkyl group and/or a phenyl group, or a halogen atom; $R^7$ and $R^8$ are each independently a hydrogen atom, a $C_{1-5}$ alkyl group, a $C_{1-5}$ haloalkyl group, or a $C_{6-10}$ aryl group; and $Ar^1$ is a divalent organic group of formula ($Ar^1$-a) or formula ($Ar^1$-b):

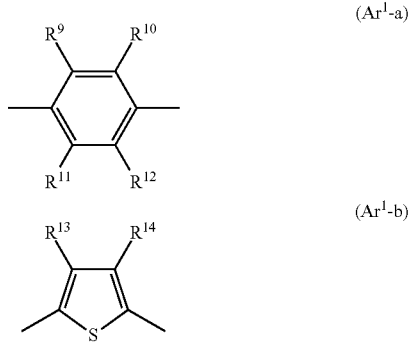

in the formula, $R^9$ to $R^{14}$ are each independently a hydrogen atom, a $C^{1-10}$ alkyl group optionally having a substituent, or a $C_{6-10}$ aryl group.

4. The cladding material according to claim 1, wherein the repeating unit is represented by formula (13):

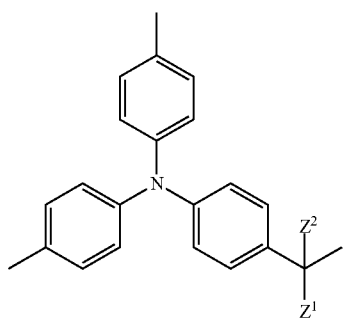

in the formula, $Z^1$ and $Z^2$ are the same as $Z^1$ and $Z^2$ above.

5. An optical waveguide comprising:
a core; and
a cladding that surrounds an entire periphery of the core and has a refractive index smaller than a refractive index of the core, wherein
the cladding is formed of the cladding material as claimed in claim 1.

6. The optical waveguide according to claim 5, wherein the core contains a nonlinear optical compound having a tricyano-bonded furan ring of formula (1) or a derivative of the nonlinear optical compound,

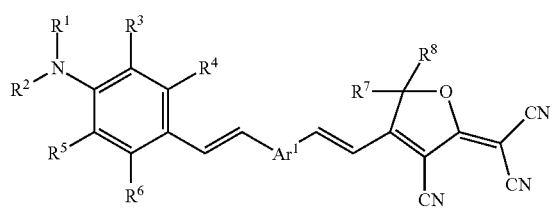

in the formula, $R^1$ and $R^2$ are each independently a hydrogen atom, a $C_{1-10}$ alkyl group optionally having a substituent, or a $C_{6-10}$ aryl group; $R^3$ to $R^6$ are each independently a hydrogen atom, a $C_{1-10}$ alkyl group, a hydroxy group, a $C_{1-10}$ alkoxy group, a $C_{2-11}$ alkylcarbonyloxy group, a $C_{6-10}$ aryloxy group, a C7-11 arylcarbonyloxy group, a silyloxy group having a $C_{1-6}$ alkyl group and/or a phenyl group, or a halogen atom; $R^7$ and $R^8$ are each independently a hydrogen atom, a $C_{1-5}$ alkyl group, a $C_{1-5}$ haloalkyl group, or a $C_{6-10}$ aryl group; and $Ar^1$ is a divalent organic group of formula ($Ar^1$-a) or formula ($Ar^1$-b):

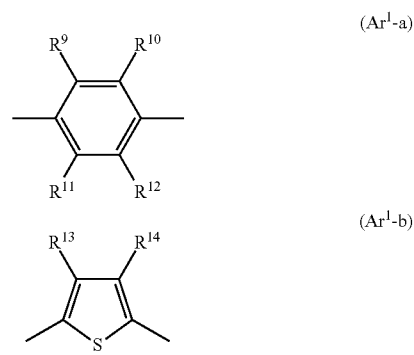

in the formula, $R^9$ to $R^{14}$ are each independently a hydrogen atom, a $C_{1-10}$ alkyl group optionally having a substituent, or a $C_{6-10}$ aryl group.

7. A production method of the optical waveguide as claimed in claim 6 having the core and the cladding that surrounds the periphery of the core and has a refractive index smaller than a refractive index of the core, the production method comprising:
a step of forming a lower cladding using the cladding material comprising:
a polymer compound including a triarylamine structure; and
a nonlinear optical compound
a step of forming on the lower cladding the core containing the nonlinear optical compound having the tricyano-bonded furan ring of formula (1) or the derivative of the nonlinear optical compound; and
a step of forming an upper cladding on the core using the cladding material as in claim 1, wherein
the production method includes, before and/or after the step of forming of the upper cladding, a step of performing a polarization orientation process on the nonlinear optical compound or the derivative of the nonlinear optical compound contained in the core.

8. A production method of a ridge-type optical waveguide that is a production method of the optical waveguide as claimed in claim 6 having the core and the cladding that surround the periphery of the core and has a refractive index smaller than a refractive index of the core, the production method comprising:
a step of forming a lower cladding using the cladding a step of forming a lower cladding using the cladding material comprising:
a polymer compound including a triarylamine structure; and
a nonlinear optical compound
a step of forming a resist layer having photosensitivity to ultraviolet rays on the lower cladding, radiating ultraviolet light onto a surface of the resist layer through a photomask and carrying out development to form a mask pattern of the core, transferring a core pattern to the lower cladding using the mask pattern as a mask, and removing the resist layer;

a step of forming on the lower cladding the core containing the nonlinear optical compound having the tricyano-bonded furan ring of formula (1) or the derivative of the nonlinear optical compound; and a step of forming an upper cladding on the core using the cladding material, wherein the production method includes, before and/or after the step of forming of the upper cladding, a step of performing a polarization orientation process on the nonlinear optical compound or the derivative of the nonlinear optical compound contained in the core.

9. The production method according to claim 7, in that the polarization orientation process is an electric field applying process with electrodes.

10. A polymer compound having a repeating unit of formula (2) or formula (3):

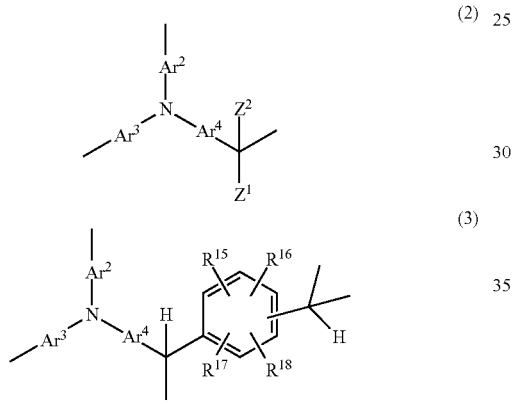

in formula (2) and formula (3), $Ar^2$ to $Ar^4$ are each independently any one of divalent organic groups of formulae (4) to (8) below; in formula (2), $Z^1$ is a monovalent organic group of formula (9) below, and $Z^2$ is a hydrogen atom; and in formula (3), $R^{15}$ to $R^{18}$ are each independently a hydrogen atom; $R^{15}$ to $R^{18}$ are not simultaneously hydrogen atoms or a $C_{1-5}$ hydroxyalkyl group,

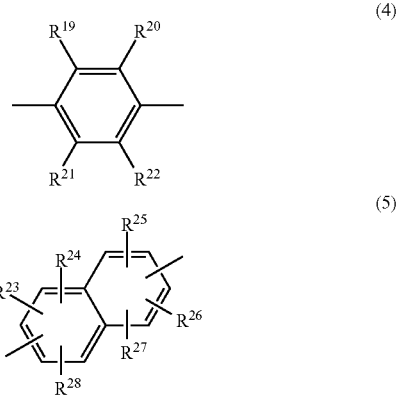

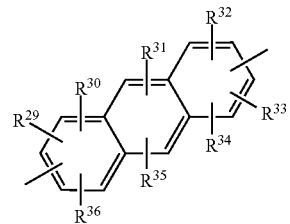

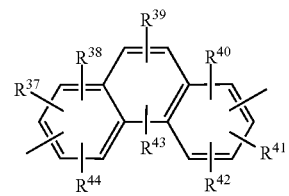

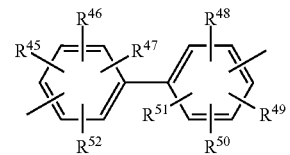

in the formula, $R^{19}$ to $R^{52}$ are each independently a hydrogen atom, a $C_{1-5}$ alkyl group, an epoxy group, a carboxy group, a hydroxy group, a $C_{1-5}$ alkoxy group, or a halogen atom,

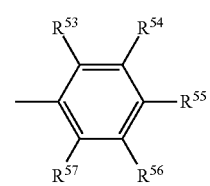

in the formulas, $R^{19}$ to $R^{52}$ are each independently a hydrogen atom, a $C_{1-5}$ alkyl group, an epoxy group, a carboxy group, a hydroxy group, a $C_{1-5}$ alkoxy group, or a halogen atom, in the formula, $R^{53}$ to $R^{57}$ are each independently a hydrogen atom (provided that $R^{53}$ to $R^{57}$ are not simultaneously hydrogen atoms), a $C_{1-5}$ hydroxyalkyl group, an $OR^{77}$ group, a $COR^{77}$ group, a $COOR^{77}$ group, or an $NR^{77}R^{78}$ group (in these formulae, $R^{77}$ is a $C_{1-5}$ hydroxyalkyl group and $R^{78}$ is a hydrogen atom).

11. The polymer compound according to claim 10, wherein the repeating unit is represented by formula (13):

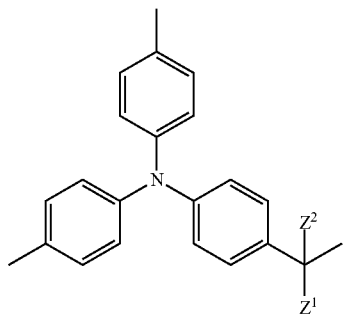
in the formula, Z and $Z^2$ are the same as Z1 and $Z^2$ above.
* * * * *